US009474799B2

(12) United States Patent
Robinson et al.

(10) Patent No.: US 9,474,799 B2
(45) **Date of Patent: *Oct. 25, 2016**

(54) FUNCTIONAL INFLUENZA VIRUS-LIKE PARTICLES (VLPS)

(71) Applicant: NOVAVAX, INC., Gaithersburg, MD (US)

(72) Inventors: Robin A. Robinson, Dickerson, MD (US); Peter M. Pushko, Frederick, MD (US)

(73) Assignee: Novavax, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/700,577

(22) Filed: Apr. 30, 2015

(65) Prior Publication Data

US 2015/0306206 A1 Oct. 29, 2015

Related U.S. Application Data

(63) Continuation of application No. 13/796,125, filed on Mar. 12, 2013, now Pat. No. 9,144,607, which is a continuation of application No. 10/617,569, filed on Jul. 11, 2003, now Pat. No. 8,592,197.

(51) Int. Cl.

| | |
|---|---|
| ***A61K 39/145*** | (2006.01) |
| ***C07H 21/04*** | (2006.01) |
| ***C07K 14/005*** | (2006.01) |
| ***C12N 7/00*** | (2006.01) |
| ***A61K 39/12*** | (2006.01) |
| *A61K 39/00* | (2006.01) |

(52) U.S. Cl.

CPC ............. *A61K 39/145* (2013.01); *A61K 39/12* (2013.01); *C07H 21/04* (2013.01); *C07K 14/005* (2013.01); *C12N 7/00* (2013.01); *A61K 2039/5258* (2013.01); *C12N 2760/16023* (2013.01); *C12N 2760/16034* (2013.01); *C12N 2760/16122* (2013.01); *C12N 2760/16123* (2013.01); *C12N 2760/16134* (2013.01)

(58) Field of Classification Search

None

See application file for complete search history.

(56) References Cited

U.S. PATENT DOCUMENTS 4,552,758 A 11/1985 Murphy et al.
6,224,882 B1 5/2001 Smith et al.
6,649,372 B1 11/2003 Palese et al.
7,556,940 B2 7/2009 Galarza et al.
7,763,450 B2 7/2010 Robinson et al.
8,080,255 B2 * 12/2011 Smith .................. A61K 39/145 424/205.1
8,506,967 B2 * 8/2013 Smith .................. A61K 39/145 424/205.1
8,551,756 B2 10/2013 Smith et al.
8,592,197 B2 * 11/2013 Robinson ............. A61K 39/145 424/204.1
8,951,537 B2 * 2/2015 Smith .................. A61K 39/145 424/209.1
8,992,939 B2 3/2015 Smith et al.
9,050,290 B2 * 6/2015 Smith .................. A61K 39/145
9,144,607 B2 9/2015 Robinson et al.
9,180,180 B2 11/2015 Smith et al.
2003/0035814 A1 2/2003 Kawaoka et al.
2005/0009008 A1 1/2005 Robinson et al.
2006/0263804 A1 11/2006 Robinson et al.
2007/0184526 A1 8/2007 Smith et al.
2010/0129401 A1 5/2010 Smith et al.
2012/0207786 A1 8/2012 Smith et al.
2013/0039938 A1 2/2013 Smith et al.
2013/0177587 A1 * 7/2013 Robinson ............. A61K 39/145 424/192.1
2013/0295135 A1 11/2013 Smith et al.
2014/0193447 A1 7/2014 Smith et al.
2015/0307849 A1 10/2015 Smith et al.
2015/0374813 A1 12/2015 Smith et al.

FOREIGN PATENT DOCUMENTS

EP 0870508 A1 10/1998
EP 1644037 B1 12/2011
WO WO 95/22989 A1 8/1995
WO WO 96/10633 A1 4/1996
WO WO 96/37624 A1 11/1996

(Continued)

OTHER PUBLICATIONS

"New Strain of Avian Influenza Now Found to Infect Humans," Medscape [online] (Mar. 22, 2006) htttp://www.medscape.com/viewarticle/528258_print.

(Continued)

*Primary Examiner* — Shanon A Foley
*Assistant Examiner* — Myron Hill
(74) *Attorney, Agent, or Firm* — Cooley LLP; Fraser D. Brown

(57) ABSTRACT

Recombinant influenza virus proteins, including influenza capsomers, subviral particles, virus-like particles (VLP), VLP complexes, and/or any portions of thereof, are provided as a vaccine for influenza viruses. The invention is based on the combination of two vaccine technologies: (1) intrinsically safe recombinant vaccine technology, and (2) highly immunogenic, self-assembled protein macromolecules embedded in plasma membranes and comprised of multiple copies of influenza virus structural proteins exhibiting neutralizing epitopes in native conformations. More specifically, this invention relates to the design and production of functional homotypic and heterotypic recombinant influenza virus-like particles (VLPs) comprised of recombinant structural proteins of human influenza virus type A/Sydney/5/94 (H3N2) and/or avian influenza virus type A/Hong Kong/1073/99 (H9N2) in baculovirus-infected insect cells and their application as a vaccine in the prevention of influenza infections and as a laboratory reagent for virus structural studies and clinical diagnostics.

10 Claims, 13 Drawing Sheets

(56) References Cited

FOREIGN PATENT DOCUMENTS

| | | | |
|---|---|---|---|
| WO | WO 01/00684 A1 | 1/2001 |
| WO | WO 02/00885 A2 | 1/2002 |
| WO | WO 03/048348 A2 | 6/2003 |
| WO | WO 03/051835 A2 | 6/2003 |
| WO | WO 2005/020889 A2 | 3/2005 |

OTHER PUBLICATIONS

"Section 1. Past Achievements and Future Needs," Vaccines, Vaccination and the Immune Response, pp. 1-45, by Gordon Ada, Alistair Ramsay (1997).
Ali et al., "Influenza Virus Assembly: Effect of Influenza Virus Glycoproteins on the Membrane Association of M1 Protein," J. Virol. 74:8709-8719 (2000).
Avalos et al., "Association of Influenza Virus NP and M1 Proteins with Cellular Cytoskeletal Elements in Influenza Virus-Infected Cells," J. Virol. 71:2947-2958 (1997).
Belser et al., "The ferret as a model organism to study influenza A virus infection," Dis. Model. Mech. 4(5):575-579 (2011).
Bender et al., "Characterization of the Surface Proteins of Influenza A (H5N1) Viruses Isolated from Humans in 1997-1998," Virology 254:115-123 (1999).
Berglund et al., "Immunization with Recombinant Semlike Forest Virus Induces Protection Against Influenza Challenge in Mice," Vaccine 17:497-507 (1999).
Bright et al., "Cross-Clade Protective Immune Responses to Influenza Viruses with H5N1 HA and NA Elicited by an Influenza Virus-Like Particle," PLOS One, Public Library of Science 3:1501 (2008).
Bucher et al., "Incorporation of Influenza Virus M-Protein into Liposomes," J. Virol. 36:586-590 (1980).
Bucher et al., "M Protein (M1) of Influenza Virus: Antigenic Analysis and Intracellular Localization with Monoclonal Antibodies," J. Virol. 63:3622-3633 (1989).
Bullido et al., "Several Protein Regions Contribute to Determine the Nuclear and Cytoplasmic Localization of the Influenza A Virus Nucleoprotein," J. Gen. Virol. 81:135-142 (2000).
Castrucci et al., "Reverse Genetics System for Generation of an Influenza A Virus Mutant Containing a Deletion of the Carboxyl-Terminal Residue of M2 Protein," J. Virol. 69:2725-2728 (1995).
Chambers et al., "A single dose of killed *Mycobacterium bovis* BCG in a novel class of adjuvant (Novasome™) protects guinea pigs from lethal tuberculosis," Vaccine 22:1063-1071 (2004).
Chen et al., "Avian flu: H5N1 virus outbreak in migratory waterfowl," Nature 436:191-192 (2005).
Chen et al., "Comparison of the ability of viral protein-expressing plasmid DNAs to protect against influenza," Vaccine 16:1544-1549 (1998).
Chen et al., "Enhanced protection against a lethal influenza virus challenge by immunization with both hemagglutinin- and neuraminidase-expressing DNAs," Vaccine 17:653-659 (1999).
Chen et al., "The Evolution of H5N1 Influenza Viruses in Ducks in Southern China," Proc. Natl. Acad. Sci. USA 101:10452-10457 (2004).
Cox and Coulter, "Adjuvants—A Classification and Review of Their Modes of Action," Vaccine 15:248-256 (1997).
Crawford et al., "Baculovirus-Derived Hemagglutinin Vaccines Protect Against Lethal Influenza Infections by Avian H5 and H7 Subtypes," Vaccine 17:2265-2274 (1999).
Crowther et al., "Three-Dimensional Structure of Hepatitis B. Virus Core Particles Determined by Electron Cryomicroscopy," Cell 77:943-950 (1994).
Das et al., "Structural basis for suppression of a host antoviral response by influenza A virus," Proc. Natl. Acad. Sci. USA 105:13093-13098 (2008).
Database UniProt [Online] Oct. 1, 2004, Hongbo Z et al.: "Matrix protein 1" XP002526328 retrieved from http://www.uniprot.org/uniprot/q6b3p4 Database accession No. Q6B3P4.
Database UniProt [Online] Jul. 11, 2006, Hoffmann E et al.: "Hemagglutinin" XP002526332 retrieved from http://www.uniprot.org/uniprot/q195d4 Database accession No. Q195D4.
Database UniProt [Online] Sep. 13, 2005, Chen H et al.: "Neuramidase" XP002526329 retrieved from http://www.uniprot.org/uniprot/q4fb59 Database accession No. Q4FB59.
Database UniProt [Online] Aug. 16, 2004, Li KS et al.: "Hemagglutinin" XP002526330 retrieved from http://www.uniprot.org/uniprot/q6dq47 Database accession No. Q6DQ47.
Database UniProt Oct. 25, 2004, Li KS et al.: "Neuramidase" XP002526331 retrieved from http://www.uniprot.org/uniprot/q6dph6 Database accession No. Q6DPH6.
Ebel, Search Report and Written Opinion, 9 pages, from Singapore Patent Appl. No. 200701731-2 (mailed Feb. 25, 2010).
Elster et al., "Influenza Virus MI Protein Binds to RNA Through Its Nuclear Localization Signal", J. Gen. Virol. 78:1589-1956 (1997).
Enami and Enami, "Influenza Virus Hemagglutinin and Neuraminidase Glycoproteins Stimulate the Membrane Association of the Matrix Protein," J. Virol. 70:6653-6657 (1996).
Fodor et al., "Rescue of Influenza A Virus from Recombinant DNA," J. Virol. 73:9679-9682 (1999).
Galarza et al., "Virus-Like Particle (VLP) Conferred Complete Protection Against a Lethal Influenza Virus Challenge," Viral Immunol 18:244-251 (2005).
Galarza et al., "Virus-Like Particle Vaccine Conferred Complete Protection Against a Lethal Influenza Virus Challenge," Viral Immunol 18:365-372 (2005).
Germann et al., "Mitigation Strategies for Pandemic Influenza in the United States," Proc. Natl. Acad. Sci. USA 103:5935-5940 (2006).
Gómez-Puertas et al., "Efficient Formation of Influenza Virus-Like Particles: Dependence on the Expression Levels of Viral Proteins," J. Gen. Virol. 80:1635-1645 (1999).
Gómez-Puertas et al., "Influenza Virus Matrix Protein is the Major Driving Force in Virus Budding," J. Virol. 74:11538-11547 (2000).
Gregoriadis et al., "Vaccine Entrapment in Liposomes," Methods 19:156-162 (1999).
Gupta et al., "Adjuvant properties of non-phospholipid liposomes (Novasomes) in experimental animals for human vaccine antigens," Vaccine 14:219-225 (1996).
Hatta and Kawaoka, "A clue to the molecular mechanism of virulence of highly pathogenic H5N1 avian influenza viruses isolated in 2004," Virus 55:55-62 (2005).
Hatta et al., "Special topic, Mechanism of infection, Mechanism of defense, Pathogenesis of Hong Kong H5N1 influenza virus, Why did avian influenza viruses affected humans?" Cell Technol. 21(2):192-197 (2002).
Heiduschat, "Supplementary European Search Report," 12 pages, from EP Appl. No. 06826264.1, European Patent Office, Munich, Germany (mailed May 28, 2009).
Hirata Clinic, "Influenza Q&A," http://web.archive.org/web/20010427013049//http://www5a.big1obe.ne.jp/~hiracli/QA.htm (2001).
Hoffmann et al., "A DNA Transfection System for Generation of Influenza A Virus from Eight Plasmids," Proc. Natl. Acad. Sci. USA 97:6108-6113 (2000).
Huylebroeck et al., "High-level transient expression of influenza virus proteins from a series of SV40 late and early replacement vectors," Gene 66:163-181 (1988).
Itamura, "Development of influenza vaccines against newly emerging A/H5N1 virus," Nippon Rinsho 58:255-264 (2000).
Johansson, "Immunization with Influenza A Virus Hemagglutinin and Neuraminidase Produced in Recobinant Baculovirus Results in a Balanced and Broadened Immune Response Superior to Conventional Vaccine," Vaccine 17:2073-2080 (1999).
Korsman, "Vaccines," Chapter 6, pp. 127-149 in: Influenza Report 2006; Eds. Bernd Sebastian Kamps, Christian Hoffmann and Wolfgang Preiser; Mar. 24, 2006.
Kretzschmar et al., "Membrane Association of Influenza Virus Matrix Protein Does Not Require Specific Hydrophobic Domains or the Viral Glycoproteins," Virol. 220:37-45 (1996).
Kuroda et al., "Expression of the Influenza virus Haemagglutinin in Insect Cells by a Baculovirus Vector," EMBO J. 5:1359-1365 (1986).

(56) References Cited

OTHER PUBLICATIONS

Lakey et al., "Recombinant Baculovirus Influenza A Hemagglutinin Vaccines are Well Tolerated and Immunogenic in Healthy Adults" J. Infect. Dis. 174:838-841 (1996).
Latham and Galarza, "Formation of Wild-Type and Chimeric Influenza Virus-Like Particles Following Simultaneous Expression of Only Four Structural Proteins," J. Virol. 75:6154-6165 (2001).
Li et al., "Chimeric Influenza Virus Induces Neutralizing Antibodies and Cytotoxic T Cells Against Human Immunodeficiency Virus Type 1," J. Virol. 67:6659-6666 (1993).
Li et al., "Genesis of a highly pathogenic and potentially pandemic H5N1 influenza virus in eastern Asia," Nature 430:209-213 (2004).
Li et al., "Recombinant Influenza A Virus Vaccines for the Pathogenic Human A/Hong Kong/97 (H5N1 Viruses," J. Infect. Dis. 179:1132-1138 (1999).
Li et al., Matrix protein 1 [Influenza A virus (A/Dk/HN/5806/2003(H5N1))], Genbank AAT70589.1 published on Jul. 16, 2004.
Lin et al., "Avian-to-human transmission of H9N2 subtype influenza A viruses: Relationship between H9N2 and H5N1 human isolates," Proc. Natl. Acad. Sci. USA 97(17):9654-9658 (2000).
Logrippo, "Investigations of the use of beta-propiolactone in virus inactivation," Ann. N.Y. Acad. Sci. 83:578-594 (1960).
Lyles et al. "Subunit Interactions of Vesicular Stomatitis Virus Envelope Glycoprotein Stablilized by Binding to Viral Matrix Protein," J. Virol. 66:349-358 (1992).
Matassov et al., "A Novel intranasal Virus-Like Particle (VLP) Vaccine Designed to Protect against the Pandemic 1918 Influenza A Virus (H1N1)," Viral Immunol. 20:441-452 (2007).
Matsuda, "Notice of Reasons for Rejection," 3 pages, Japan Patent Appl. No. 2006-518925, with 4 page translation (mailed Mar. 17, 2010).
Mena et al., "Rescue of a Synthetic Chloramphenicol Acetyltransferase RNA into Influenza Virus-Like Particles Obtained from Recombinant Plasmids," J. Virol. 70:5016-5024 (1996).
Murphy and Webster, Orthomyxoviruses, Fields Virology, Third Edition, vol. 1, pp. 1397-1445 (1996).
NCBI Accession No. CY014173, "Influenza A virus (A/Indonesia/5/2005 (H5N1)) segment 7 sequence," 3 pages (available Aug. 30, 2006).
Nerome et al., "Development of a new type of influenza subunit vaccine made by muramyldipeptide-liposome: enhancement of humoral and cellular immune responses," Vaccine 8:503-509 (1990).
Neumann et al., "An Improved Reverse Genetics System for Influenza A Virus Generation and its Implications for Vaccine Production," Proc. Natl. Acad. Sci. USA 102:16825-16829 (2005).
Neumann et al., "Generation of Influenza A Viruses Entirely from Cloned cDNAs," Proc. Natl. Acad. Sci. USA 96:9345-9350 (1999).
Neumann et al., "Plasmid-Driven Formation of Influenza Virus-Like Particles," J. Virol. 74:547-551 (2000).
Olsen et al., "Immunogenicity and Efficacy of Baculovirus-Expressed and DNA-Based Equine Influenza Virus Hemagglutinin Vaccines in Mice," Vaccine 15:1149-1156 (1997).
Ottolini et al,. "The cotton rat provides a useful small-animal model for the study of influenza virus pathogenesis," J. Gen. Virol. 86(Pt 10):2823-2830 (2005).
Palese, "Making Better Influenza Vaccines?" Emerg. Infect. Dis. 12:61-65 (2006).
Park et al., "The M2 Ectodomain Is Important for Its Incorporation into Influenza A Virions," J. Virol. 72(3):2449-2455 (1998).
Park, Man-Seong, et al., "Engineered Viral Vaccine Constructs with Dual Specificity: Avian Influenza and Newcastle Disease," Proc. Natl. Acad. Sci. USA 103:8203-8208 (2006).
Pattnaik et al., "Formation of Influenza Virus particles Lacking Hemagglutinin on the Viral Envelope," J. Virol. 60:994-1001 (1986).
Peiris et al., "Cocirculation of Avian H-N2 and Contemporary "Human" H3N2 Influenza A Viruses in Pigs in Southeastern China: Potential for Genetic Reassortment?" J. Virol. 75:9679-9686 (2001).
Peradze et al., "Anti-influenza prophylactic formulations," 1986, Moscow, Meditsina, pp. 218-225.
Piedra et al., "Herd Immunity in Adults Against Influenza-Related Illnesses with use of the Trivalent-Live Attenuated Influenza Vaccine (CAIV-T) in Children," Vaccine 23:1540-1548 (2005).
Pleschka et al., "A Plasmid-Based Reverse Genetics System for Influenza A Virus," J. Virol. 70:4188-4192 (1996).
Plotnicky et al., "The immunodominant influenza matrix T cell epitope recognized in human induces influenza protection in HLA-A2/$K^b$ transgenic mice," Virology 309:320-329 (2003).
Pumpens and Grens, "Artificial Genes for Chimeric Virus-Like Particles," Artificial DNA (Khudyakov, Y.E., and Fields, H.A., Eds.) pp. 249-327, CRC Press, New York (2003).
Pushko et al., "Influenza Virus-Like Particles Comprised of the HA, NA, and M1 proteins of H9N2 Influenza Virus Induce Protective Immune Responses in BALB/c Mice," Vaccine 23:5751-5759 (2005).
Pushko et al., "Replicon-Helper Systems from Attenuated Venezuelan Equine Encephalitis Virus: Expression of Heterologous Genes in Vitro and Immunization Against Heterologous Pathogens in Vivo," Virology 239:389-401 (1997).
Saito et al., "Characterization of a human H9N2 influenza virus isolated in Hong Kong," Vaccine 20:125-133 (2001).
Slepushkin et al., "Protection of Mice Against Influenza A Virus Challenge by Vaccination With Baculovirus-Expressed M2 Protein," Vaccine 13:1399-1402 (1995).
Smith et al., U.S. Appl. No. 12/558,844, filed Sep. 14, 2009.
Smith et al., U.S. Appl. No. 12/832,657, filed Jul. 8, 2010.
St. Angelo et al., "Two of the Three Influenza Viral Polymerase Proteins Expressed by Using Baculovirus Vectors Form a Complex in Insect Cells," J. Virol. 61:361-365 (1987).
The Patent Office of the People's Republic of China, "The Decision of Final Rejection of the Application," 4 pages, from China Patent Appl. No. 200480026152.3 (issued May 20, 2010).
Tian et al., "Study and Use of Avian Flu H5 and H9 Bivalent Inactivated Vaccines (Strains H5N1 Re-1 and H9N2 Re-2)," Symposia of the 6th Symposium of the Branch of Biotechnology of Veterinary and Animal Husbandry of Chinese Association of Animal Science and Veterinary Medicine and the Branch of Veterinary Immunology of Chinese Society for Immunologypp. 42-47 (2005).
Tobita et al., "Spontaneous Excretion of Virus from MDCK Cells Persistently Infected with Influenza Virus A/PR/8/34," J. Gen. Virol. 78:563-566 (1997).
Treanor et al., "Evaluation of a Recombinant Hemagglutinin Expressed in Insect Cells as an Influenza Vaccine in Young an Elderly Adults," J. Infect. Dis. 173:1467-1470 (1996).
Treanor et al., "Safety and Immunogenicity of an Inactivated Subvirion Influenza A (H5N1) Vaccine," N. Engl. J. Med. 354:1343-1351 (2006).
Tsuji et al, "Recombinant Sindbis Viruses Expressing a Cytotoxic T-Lymphocyte Epitope of a Malaria Parasite or of Influenza Virus Elicit Protection Against the Corresponding Pathogen in Mice," J. Virol. 72:6907-6910 (1998).
Ulmer et al., "Heterologous Protection Against Influenza by Injection of DNA Encoding a Viral Protein," Science 259:1745-1749 (1993).
Ulmer et al., "Protective CD4+ and CD8+ T Cells against Influenza Virus Induced by Vaccination with Nucleoprotein DNA," J. Virol. 72:5648-5653 (1998).
Unknown, Rinsho to Kenkyuu 81:1899-1903 (2004).
Watanabe et al., "Immunogenicity and Protective Efficacy of Replication-Incompetent Influenza Virus-Like Particles," J. Virol. 76:767-773 (2002).
Watatabe et al., "Influenza A Virus Can Undergo Multiple Cycles of Replication without M2 Ion Channel Activity," J. Virol. 75(12):5656-5662 (2001).
Welsh, "Examiner's first report on patent application No. 2004268510," 3 pages, from Australian Patent Appl. No. 2004268510 (dated Feb. 5, 2010).
Wiebke, "Communication pursuant to Article 94(3) EPC," 4 pages, from EP Appl. No. 04786052.3, European Patent Office, Munich, Germany (mailed Mar. 19, 2010).

(56) References Cited

OTHER PUBLICATIONS

Wiebke, "Communication pursuant to Article 94(3) EPC," 7 pages, from EP Appl. No. 04786052.3, European Patent Office, Munich, Germany (mailed Sep. 15, 2008).
Wiebke, "European Search Report," 8 pages, from EP Appl. No. 10010286.2, European Patent Office, Munich, Germany (mailed May 23, 2011).
Wiebke, "Supplementary European Search Report," 6 pages, from EP Appl. No. 04786052.3, European Patent Office, Munich, Germany (mailed Mar. 26, 2008).
Wood et al., "Preparation of Vaccines Against H5N1 Influenza," Vaccine, 20:S84-S87 (2002).
Yasuda et al., "Growth Control of Influenza A Virus by MI Protein: Analysis of Transfectant Viruses Carrying the Chimeric M Gene," J. Virol. 68:8141-8146 (1994).
Ye et al., "Nucleus-Targeting Domain of the Matrix Protein (MI) of Influenza Virus," J. Virol. 69:1964-1970 (1995).
Zhang and Lamb, "Characterization of the Membrane Association of the Influenza Virus Matrix Protein in Living Cells," Virol. 225:225-266 (1996).
Zhao et al., "The M1 and NP Proteins of Influenza A Virus Form Homo- but not Heterooligomeric Complexes when Coexpressed in BHK-21 Cells," J. Gen. Virol. 79:2435-2446 (1998).
Zhou et al., "Generation of Cytotoxic and Humoral Immune-Responses by Non-replicative Recombinant Semlike Forest Virus," Proc. Natl. Acad. Sci. USA 92:3009-3013 (1995).
Zitzow et al., "Pathogenesis of Avian Influenza A (H5N1) Viruses in Ferrets," J. Virol. 76(9):4420-4439 (2002).
Burleigh et al., "Influenza A Viruses with Mutations in the M1 Helix Six Domain Display a Wide Variety of Morphological Phenotypes," J. Virol. 79(2):1262-1270 (2005).
Roldao et al., "Virus-like particles in vaccine development." Expert Rev. Vaccines 9(10):1149-1176 (2010).
Search Report, SG appl. No. 2014012868, 7 pages (Feb. 15, 2016).
UniProt Accession No. Q6DPY4 Matrix protein 1 of Influenza A virus A/Ck/Indonesia/4/2004(H5N1)), Aug. 16, 2004, 6 pages, http://www.uniprot.org/uniprot/Q6DPY4.
UniProt Accession No. Q1WDM0, Hemagglutinin of Influenza A virus (A/Anhui/1/2005(H5N1)), May 2, 2006, http://www.uniprot.org/uniprot/Q1WDM0.
UniProt Accession No. Q4FB63, Neuraminidase of Influenza A virus (A/Barheaded Goose/Qinghai/60/05(H5N1)), Aug. 30, 2005, http://www.uniprot.org/uniprot/Q4FB63.
Written Opinion, SG appl. No. 2014012868, 7 pages (Feb. 15, 2016).

* cited by examiner

ATGAATCCAAATCAAAAGATAATAGCACTTGGCTCTGTTTCTATAACTATTGCGACAATATG
TTTACTCATGCAGATTGCCATCTTAGCAACGACTATGACACTACATTTCAATGAATGTACCA
ACCCATCGAACAATCAAGCAGTGCCATGTGAACCAATCATAATAGAAAGGAACATAACAGAG
ATAGTGCATTTGAATAATACTACCATAGAGAAGGAAAGTTGTCCTAAAGTAGCAGAATACAA
GAATTGGTCAAAACCGCAATGTCAAATTACAGGGTTCGCCCCTTTCTCCAAGGACAACTCAA
TTAGGCTTTCTGCAGGCGGGGATATTTGGGTGACAAGAGAACCTTATGTATCGTGCGGTCTT
GGTAAATGTTACCAATTTGCACTTGGGCAGGGAACCACTTTGAACAACAAACACTCAAATGG
CACAATACATGATAGGAGTCCCCATAGAACCCTTTTAATGAACGAGTTGGGTGTTCCATTTC
ATTTGGGAACCAAACAAGTGTGCATAGCATGGTCCAGCTCAAGCTGCCATGATGGGAAGGCA
TGGTTACATGTTTGTGTCACTGGGGATGATAGAAATGCGACTGCTAGCATCATTTATGATGG
GATGCTTACCGACAGTATTGGTTCATGGTCTAAGAACATCCTCAGAACTCAGGAGTCAGAAT
GCGTTTGCATCAATGGAACTTGTACAGTAGTAATGACTGATGGAAGTGCATCAGGAAGGGCT
GATACTAAAATACTATTCATTAGAGAAGGGAAAATTGTCCACATTGGTCCACTGTCAGGAAG
TGCTCAGCATGTGGAGGAATGCTCCTGTTACCCCCGGTATCCAGAAGTTAGATGTGTTTGCA
GAGACAATTGGAAGGGCTCCAATAGACCCGTGCTATATATAAATGTGGCAGATTATAGTGTT
GATTCTAGTTATGTGTGCTCAGGACTTGTTGGCGACACACCAAGAAATGACGATAGCTCCAG
CAGCAGTAACTGCAGGGATCCTAATAACGAGAGAGGGGGCCCAGGAGTGAAAGGGTGGGCCT
TTGACAATGGAAATGATGTTTGGATGGGACGAACAATCAAGAAAGATTCGCGCTCTGGTTAT
GAGACTTTCAGGGTCGTTGGTGGTTGGACTACGGCTAATTCCAAGTCACAAATAAATAGGCA
AGTCATAGTTGACAGTGATAACTGGTCTGGGTATTCTGGTATATTCTCTGTTGAAGGAAAAA
CCTGCATCAACAGGTGTTTTTATGTGGAGTTGATAAGAGGGAGACCACAGGAGACCAGAGTA
TGGTGGACTTCAAATAGCATCATTGTATTTTGTGGAACTTCAGGTACCTATGGAACAGGCTC
ATGGCCCGATGGAGCGAATATCAATTTCATGTCTATATAA

FIGURE 1

ATGGAAACAATATCACTAATAACTATACTACTAGTAGTAACAGCAAGCAATGCAGATAAAAT
CTGCATCGGCCACCAGTCAACAAACTCCACAGAAACTGTGGACACGCTAACAGAAACCAATG
TTCCTGTGACACATGCCAAAGAATTGCTCCACACAGAGCATAATGGAATGCTGTGTGCAACA
AGCCTGGGACATCCCCTCATTCTAGACACATGCACTATTGAAGGACTAGTCTATGGCAACCC
TTCTTGTGACCTGCTGTTGGGAGGAAGAGAATGGTCCTACATCGTCGAAAGATCATCAGCTG
TAAATGGAACGTGTTACCCTGGGAATGTAGAAAACCTAGAGGAACTCAGGACACTTTTTAGT
TCCGCTAGTTCCTACCAAAGAATCCAAATCTTCCCAGACACAACCTGGAATGTGACTTACAC
TGGAACAAGCAGAGCATGTTCAGGTTCATTCTACAGGAGTATGAGATGGCTGACTCAAAAGA
GCGGTTTTTACCCTGTTCAAGACGCCCAATACACAAATAACAGGGGAAAGAGCATTCTTTTC
GTGTGGGGCATACATCACCCACCCACCTATACCGAGCAAACAAATTTGTACATAAGAAACGA
CACAACAACAAGCGTGACAACAGAAGATTTGAATAGGACCTTCAAACCAGTGATAGGGCCAA
GGCCCCTTGTCAATGGTCTGCAGGGAAGAATTGATTATTATTGGTCGGTACTAAAACCAGGC
CAAACATTGCGAGTACGATCCAATGGGAATCTAATTGCTCCATGGTATGGACACGTTCTTTC
AGGAGGGAGCCATGGAAGAATCCTGAAGACTGATTTAAAAGGTGGTAATTGTGTAGTGCAAT
GTCAGACTGAAAAAGGTGGCTTAAACAGTACATTGCCATTCCACAATATCAGTAAATATGCA
TTTGGAACCTGCCCCAAATATGTAAGAGTTAATAGTCTCAAACTGGCAGTCGGTCTGAGGAA
CGTGCCTGCTAGATCAAGTAGAGGACTATTTGGAGCCATAGCTGGATTCATAGAAGGAGGTT
GGCCAGGACTAGTCGCTGGCTGGTATGGTTTCCAGCATTCAAATGATCAAGGGGTTGGTATG
GCTGCAGATAGGGATTCAACTCAAAAGGCAATTGATAAAATAACATCCAAGGTGAATAATAT
AGTCGACAAGATGAACAAGCAATATGAAATAATTGATCATGAATTCAGTGAGGTTGAAACTA
GACTCAATATGATCAATAATAAGATTGATGACCAAATACAAGACGTATGGGCATATAATGCA
GAATTGCTAGTACTACTTGAAAATCAAAAAACACTCGATGAGCATGATGCGAACGTGAACAA
TCTATATAACAAGGTGAAGAGGGCACTGGGCTCCAATGCTATGGAAGATGGGAAAGGCTGTT
TCGAGCTATACCATAAATGTGATGATCAGTGCATGGAAACAATTCGGAACGGGACCTATAAT
AGGAGAAAGTATAGAGAGGAATCAAGACTAGAAAGGCAGAAAATAGAGGGGGTTAAGCTGGA
ATCTGAGGGAACTTACAAAATCCTCACCATTTATTCGACTGTCGCCTCATCTCTTGTGCTTG
CAATGGGGTTTGCTGCCTTCCTGTTCTGGGCCATGTCCAATGGATCTTGCAGATGCAACATT
TGTATATAA

FIGURE 2

ATGAGTCTTCTAACCGAGGTCGAAACGTACGTTCTCTCTATCATCCCATCAGGCCCCCTCAA
AGCCGAGATCGCGCAGAGACTTGAGGATGTTTTTGCAGGGAAGAACACAGATCTTGAGGCTC
TCATGGAATGGCTAAAGACAAGACCAATCCTGTCACCTCTGACTAAGGGGATTTTAGGGTTT
GTGTTCACGCTCACCGTGCCCAGTGAGCGAGGACTGCAGCGTAGACGATTTGTCCAAAATGC
CCTAAATGGGAATGGAGACCCAAACAACATGGACAGGGCAGTTAAACTATACAAGAAGCTGA
AGAGGGAAATGACATTCCATGGAGCAAAGGAAGTTGCACTCAGTTACTCAACTGGTGCGCTT
GCCAGTTGCATGGGTCTCATATACAACCGGATGGGAACAGTGACCACAGAAGTGGCTCTTGG
CCTAGTATGTGCCACTTGTGAACAGATTGCTGATGCCCAACATCGGTCCCACAGGCAGATGG
CGACTACCACCAACCCACTAATCAGGCATGAGAACAGAATGGTACTAGCCAGCACTACGGCT
AAGGCCATGGAGCAGATGGCTGGATCAAGTGAGCAGGCAGCAGAAGCCATGGAAGTCGCAAG
TCAGGCTAGGCAAATGGTGCAGGCTATGAGGACAATTGGGACTCACCCTAGTTCCAGTGCAG
GTCTAAAAGATGATCTTATTGAAAATTTGCAGGCTTACCAGAAACGGATGGGAGTGCAAATG
CAGAGATTCAAGTGA

FIGURE 3

SEQUENCE LISTING

<160> NUMBER OF SEQ ID NOS: 58

<210> SEQ ID NO 1
<211> LENGTH: 1404
<212> TYPE: DNA
<213> ORGANISM: Influenza virus

<400> SEQUENCE: 1
atgaatccaa atcaaaagat aatagcactt ggctctgttt ctataactat tgcgacaata 60
tgtttactca tgcagattgc catcttagca acgactatga cactacattt caatgaatgt 120
accaacccat cgaacaatca agcagtgcca tgtgaaccaa tcataataga aaggaacata 180

-continued

```
acagagatag tgcatttgaa taatactacc atagagaagg aaagttgtcc taaagtagca    240
gaatacaaga attggtcaaa accgcaatgt caaattacag ggttcgcccc tttctccaag    300
gacaactcaa ttaggctttc tgcaggcggg gatatttggg tgacaagaga accttatgta    360
tcgtgcggtc ttggtaaatg ttaccaattt gcacttgggc agggaaccac tttgaacaac    420
aaacactcaa atggcacaat acatgatagg agtccccata gaaccctttt aatgaacgag    480
ttgggtgttc catttcattt gggaaccaaa caagtgtgca tagcatggtc cagctcaagc    540
tgccatgatg ggaaggcatg gttacatgtt tgtgtcactg gggatgatag aaatgcgact    600
gctagcatca tttatgatgg gatgcttacc gacagtattg gttcatggtc taagaacatc    660
ctcagaactc aggagtcaga atgcgtttgc atcaatggaa cttgtacagt agtaatgact    720
gatggaagtg catcaggaag ggctgatact aaaatactat tcattagaga agggaaaatt    780
gtccacattg gtccactgtc aggaagtgct cagcatgtgg aggaatgctc ctgttacccc    840
cggtatccag aagttagatg tgtttgcaga gacaattgga agggctccaa tagacccgtg    900
ctatatataa atgtggcaga ttatagtgtt gattctagtt atgtgtgctc aggacttgtt    960
ggcgacacac caagaaatga cgatagctcc agcagcagta actgcaggga tcctaataac   1020
gagagagggg gcccaggagt gaaagggtgg gcctttgaca atggaaatga tgtttggatg   1080
ggacgaacaa tcaagaaaga ttcgcgctct ggttatgaga ctttcagggt cgttggtggt   1140
tggactacgg ctaattccaa gtcacaaata aataggcaag tcatagttga cagtgataac   1200
tggtctgggt attctggtat attctctgtt gaaggaaaaa cctgcatcaa caggtgtttt   1260
tatgtggagt tgataagagg gagaccacag gagaccagag tatggtggac ttcaaatagc   1320
atcattgtat tttgtggaac ttcaggtacc tatggaacag gctcatggcc cgatggagcg   1380
aatatcaatt tcatgtctat ataa                                          1404
```

<210> SEQ ID NO 2
<211> LENGTH: 1683
<212> TYPE: DNA
<213> ORGANISM: Influenza virus

<400> SEQUENCE: 2

```
atggaaacaa tatcactaat aactatacta ctagtagtaa cagcaagcaa tgcagataaa     60
atctgcatcg gccaccagtc aacaaactcc acagaaactg tggacacgct aacagaaacc    120
aatgttcctg tgacacatgc caaagaattg ctccacacag agcataatgg aatgctgtgt    180
gcaacaagcc tgggacatcc cctcattcta gacacatgca ctattgaagg actagtctat    240
ggcaaccctt cttgtgacct gctgttggga ggaagagaat ggtcctacat cgtcgaaaga    300
tcatcagctg taaatggaac gtgttaccct gggaatgtag aaaacctaga ggaactcagg    360
acacttttta gttccgctag ttcctaccaa agaatccaaa tcttcccaga cacaacctgg    420
aatgtgactt acactggaac aagcagagca tgttcaggtt cattctacag gagtatgaga    480
tggctgactc aaaagagcgg tttttaccct gttcaagacg cccaatacac aaataacagg    540
ggaaagagca ttcttttcgt gtggggcata catcacccac ccacctatac cgagcaaaca    600
aatttgtaca taagaaacga cacaacaaca agcgtgacaa cagaagattt gaataggacc    660
ttcaaaccag tgatagggcc aaggcccctt gtcaatggtc tgcagggaag aattgattat    720
tattggtcgg tactaaaacc aggccaaaca ttgcgagtac gatccaatgg gaatctaatt    780
gctccatggt atggacacgt tctttcagga gggagccatg gaagaatcct gaagactgat    840
ttaaaaggtg gtaattgtgt agtgcaatgt cagactgaaa aaggtggctt aaacagtaca    900
```

-continued

```
ttgccattcc acaatatcag taaatatgca tttggaacct gccccaaata tgtaagagtt     960

aatagtctca aactggcagt cggtctgagg aacgtgcctg ctagatcaag tagaggacta    1020

tttggagcca tagctggatt catagaagga ggttggccag gactagtcgc tggctggtat    1080

ggtttccagc attcaaatga tcaaggggtt ggtatggctg cagataggga ttcaactcaa    1140

aaggcaattg ataaaataac atccaaggtg aataatatag tcgacaagat gaacaagcaa    1200

tatgaaataa ttgatcatga attcagtgag gttgaaacta gactcaatat gatcaataat    1260

aagattgatg accaaataca agacgtatgg gcatataatg cagaattgct agtactactt    1320

gaaaatcaaa aacactcgga tgagcatgat gcgaacgtga acaatctata taacaaggtg    1380

aagagggcac tgggctccaa tgctatggaa gatgggaaag gctgtttcga gctataccat    1440

aaatgtgatg atcagtgcat ggaaacaatt cggaacggga cctataatag gagaaagtat    1500

agagaggaat caagactaga aaggcagaaa atagaggggg ttaagctgga atctgaggga    1560

acttacaaaa tcctcaccat ttattcgact gtcgcctcat ctcttgtgct tgcaatgggg    1620

tttgctgcct tcctgttctg ggccatgtcc aatggatctt gcagatgcaa catttgtata    1680

taa                                                                  1683
```

<210> SEQ ID NO 3
<211> LENGTH: 759
<212> TYPE: DNA
<213> ORGANISM: Influenza virus

<400> SEQUENCE: 3

```
atgagtcttc taaccgaggt cgaaacgtac gttctctcta tcatcccatc aggccccctc      60

aaagccgaga tcgcgcagag acttgaggat gtttttgcag ggaagaacac agatcttgag     120

gctctcatgg aatggctaaa gacaagacca atcctgtcac ctctgactaa ggggatttta     180

gggtttgtgt tcacgctcac cgtgcccagt gagcgaggac tgcagcgtag acgatttgtc     240

caaaatgccc taaatgggaa tggagaccca aacaacatgg acagggcagt taaactatac     300

aagaagctga agagggaaat gacattccat ggagcaaagg aagttgcact cagttactca     360

actggtgcgc ttgccagttg catgggtctc atatacaacc ggatgggaac agtgaccaca     420

gaagtggctc ttggcctagt atgtgccact tgtgaacaga ttgctgatgc ccaacatcgg     480

tcccacaggc agatggcgac taccaccaac ccactaatca ggcatgagaa cagaatggta     540

ctagccagca ctacggctaa ggccatggag cagatggctg gatcaagtga gcaggcagca     600

gaagccatgg aagtcgcaag tcaggctagg caaatggtgc aggctatgag gacaattggg     660

actcacccta gttccagtgc aggtctaaaa gatgatctta ttgaaaattt gcaggcttac     720

cagaaacgga tgggagtgca aatgcagaga ttcaagtga                           759
```

<210> SEQ ID NO 4
<211> LENGTH: 31
<212> TYPE: DNA
<213> ORGANISM: Influenza virus

<400> SEQUENCE: 4

```
aacggtccga tggagaaaat agtgcttctt c                                    31
```

<210> SEQ ID NO 5
<211> LENGTH: 33
<212> TYPE: DNA
<213> ORGANISM: Influenza virus

<400> SEQUENCE: 5
aaagctttta aatgcaaatt ctgcattgta acg 33

<210> SEQ ID NO 6
<211> LENGTH: 32
<212> TYPE: DNA
<213> ORGANISM: Influenza virus

<400> SEQUENCE: 6
aacggtccga tgaatccaaa tcagaagata at 32

<210> SEQ ID NO 7
<211> LENGTH: 32
<212> TYPE: DNA
<213> ORGANISM: Influenza virus

<400> SEQUENCE: 7
aaagcttcta cttgtcaatg gtgaatggca ac 32

<210> SEQ ID NO 8
<211> LENGTH: 30
<212> TYPE: DNA
<213> ORGANISM: Influenza virus

<400> SEQUENCE: 8
aacggtccga tgagtcttct aaccgaggtc 30

<210> SEQ ID NO 9
<211> LENGTH: 31
<212> TYPE: DNA
<213> ORGANISM: Influenza virus

<400> SEQUENCE: 9
aaagctttca cttgaatcgc tgcatctgca c 31

<210> SEQ ID NO 10
<211> LENGTH: 1707
<212> TYPE: DNA
<213> ORGANISM: Influenza virus

<400> SEQUENCE: 10
atggagaaaa tagtgcttct tcttgcaata gtcagtcttg ttaaaagtga tcagatttgc 60
attggttacc atgcaaacaa ttcaacagag caggttgaca caatcatgga aaagaacgtt 120
actgttacac atgcccaaga catactggaa aagacacaca acgggaagct ctgcgatcta 180
gatggagtga agcctctaat tttaagagat tgtagtgtag ctggatggct cctcgggaac 240
ccaatgtgtg acgaattcat caatgtaccg gaatggtctt acatagtgga gaaggccaat 300
ccaaccaatg acctctgtta cccagggagt ttcaacgact atgaagaact gaaacaccta 360
ttgagcagaa taaaccattt tgagaaaatt caaatcatcc ccaaaagttc ttggtccgat 420
catgaagcct catcaggagt gagctcagca tgtccatacc tgggaagtcc ctcctttttt 480
agaaatgtgg tatggcttat caaaaagaac agtacatacc caacaataaa gaaaagctac 540
aataatacca accaagaaga tcttttggta ctgtggggaa ttcaccatcc taatgatgcg 600
gcagagcaga caaggctata tcaaaaccca accacctata tttccattgg gacatcaaca 660
ctaaaccaga gattggtacc aaaaatagct actagatcca aagtaaacgg gcaaagtgga 720
aggatggagt tcttctggac aattttaaaa cctaatgatg caatcaactt cgagagtaat 780
ggaaatttca ttgctccaga atatgcatac aaaattgtca agaaagggga ctcagcaatt 840

-continued

```
atgaaaagtg aattggaata tggtaactgc aacaccaagt gtcaaactcc aatgggggcg    900

ataaactcta gtatgccatt ccacaacata caccctctca ccatcgggga atgccccaaa    960

tatgtgaaat caaacagatt agtccttgca acagggctca gaaatagccc tcaaagagag   1020

agcagaagaa aaaagagagg actatttgga gctatagcag gttttataga gggaggatgg   1080

cagggaatgg tagatggttg gtatgggtac caccatagca atgagcaggg gagtgggtac   1140

gctgcagaca aagaatccac tcaaaaggca atagatggag tcaccaataa ggtcaactca   1200

atcattgaca aaatgaacac tcagtttgag gccgttggaa gggaatttaa taacttagaa   1260

aggagaatag agaatttaaa caagaagatg gaagacgggt ttctagatgt ctggacttat   1320

aatgccgaac ttctggttct catggaaaat gagagaactc tagactttca tgactcaaat   1380

gttaagaacc tctacgacaa ggtccgacta cagcttaggg ataatgcaaa ggagctgggt   1440

aacggttgtt tcgagttcta tcacaaatgt gataatgaat gtatggaaag tataagaaac   1500

ggaacgtaca actatccgca gtattcagaa gaagcaagat taaaaagaga ggaaataagt   1560

ggggtaaaat tggaatcaat aggaacttac caaatactgt caatttattc aacagtggcg   1620

agttccctag cactggcaat catgatggct ggtctatctt tatggatgtg ctccaatgga   1680

tcgttacaat gcagaatttg catttaa                                        1707
```

<210> SEQ ID NO 11
<211> LENGTH: 1350
<212> TYPE: DNA
<213> ORGANISM: Influenza virus

<400> SEQUENCE: 11

```
atgaatccaa atcagaagat aataaccatt ggatcaatct gtatggtaat tggaatagtt     60

agcttaatgt tacaaattgg gaacatgatc tcaatatggg tcagtcattc aattcagaca    120

gggaatcaac accaagctga atcaatcagc aatactaacc ctcttactga gaaagctgtg    180

gcttcagtaa cattagcggg caattcatct ctttgcccca ttagaggatg ggctgtacac    240

agtaaggaca acaatataag gatcggttcc aaggggggatg tgtttgttat tagagagccg   300

ttcatctcat gctcccacct ggaatgcaga actttcttct tgactcaggg agccttgctg    360

aatgacaagc actccaacgg gactgtcaaa gacagaagcc ctcacagaac attaatgagt    420

tgtcctgtgg gtgaggctcc ctctccatat aactcaaggt ttgagtctgt tgcttggtca    480

gcaagtgctt gccatgatgg caccagttgg ttgacaattg gaatttctgg cccagacaat    540

gaggctgtgg ctgtattgaa atacaatggc ataataacag acactatcaa gagttggagg    600

aacaacatac tgagaactca agagtctgaa tgtgcatgtg taaatggctc ttgctttact    660

gtaatgactg atggaccaag tgatgggcag gcatcatata agatcttcaa aatggaaaaa    720

ggaaaagtgg tcaaatcagt cgaattggat gctcctaatt atcactatga ggaatgctcc    780

tgttatcctg atgccggcga aatcacatgt gtttgcaggg ataattggca tggctcaaat    840

aggccatggg tatctttcaa tcaaaatttg gagtatcaaa taggatatat atgcagtgga    900

gttttcggag acaatccacg ccccaatgat ggaacaggta gttgtggccc gatgtcccct    960

aacggggcat atggggtaaa agggttttca tttaaatacg gcaatggtgt ttggatcggg   1020

agaaccaaaa gcactaattc caggagcggc tttgaaatga tttgggatcc aaatgggtgg   1080

actggaacgg acagtagctt ttcagtgaaa caagatatag tagcaataac tgattggtca   1140

ggatatagcg ggagttttgt ccagcatcca gaactgacag gattagattg cataagacct   1200
```

-continued tgtttctggg ttgagttaat cagagggcgg cccaaagaga gcacaatttg gactagtggg 1260
agcagcatat ctttttgtgg tgtaaatagt gacactgtga gttggtcttg gccagacggt 1320
gctgagttgc cattcaccat tgacaagtag 1350

<210> SEQ ID NO 12
<211> LENGTH: 759
<212> TYPE: DNA
<213> ORGANISM: Influenza virus

<400> SEQUENCE: 12
atgagtcttc taaccgaggt cgaaacgtac gttctctcta tcatcccgtc aggccccctc 60
aaagccgaga tcgcgcagaa acttgaagat gtctttgcag gaaagaacac cgatctcgag 120
gctctcatgg agtggctgaa gacaagacca atcctgtcac ctctgactaa agggattttg 180
ggatttgtat tcacgctcac cgtgcccagt gagcgaggac tgcagcgtag acgctttgtc 240
cagaatgccc taaatggaaa tggagatcca aataatatgg atagggcagt taagctatat 300
aagaagctga aaagagaaat aacattccat ggggctaaag aggtttcact cagctactca 360
accggtgcac ttgccagttg catgggtctc atatacaaca ggatgggaac ggtgactacg 420
gaagtggctt ttggcctagt gtgtgccact tgtgagcaga ttgcagattc acagcatcgg 480
tctcacaggc agatggcaac tatcaccaac ccactaatca ggcatgaaaa cagaatggtg 540
ctggccagca ctacagctaa ggctatggag cagatggcgg gatcaagtga gcaggcagcg 600
gaagccatgg aggtcgctaa tcaggctagg cagatggtgc aggcaatgag gacaattgga 660
actcatccta actctagtgc tggtctgaga gataatcttc ttgaaaattt gcaggcctac 720
cagaaacgaa tgggagtgca gatgcagcga ttcaagtga 759

<210> SEQ ID NO 13
<211> LENGTH: 30
<212> TYPE: DNA
<213> ORGANISM: Influenza virus

<400> SEQUENCE: 13
aggatccatg aagactatca ttgctttgag 30

<210> SEQ ID NO 14
<211> LENGTH: 32
<212> TYPE: DNA
<213> ORGANISM: Influenza virus

<400> SEQUENCE: 14
aggtacctca aatgcaaatg ttgcacctaa tg 32

<210> SEQ ID NO 15
<211> LENGTH: 72
<212> TYPE: DNA
<213> ORGANISM: Influenza virus

<400> SEQUENCE: 15
ggggacaagt ttgtacaaaa aagcaggctt agaaggagat agaaccatga atccaaatca 60
aaagataata ac 72

<210> SEQ ID NO 16
<211> LENGTH: 57
<212> TYPE: DNA
<213> ORGANISM: Influenza virus

<400> SEQUENCE: 16
ggggaccact ttgtacaaga aagctgggtc ctatataggc atgagattga tgtccgc 57

<210> SEQ ID NO 17
<211> LENGTH: 38
<212> TYPE: DNA
<213> ORGANISM: Influenza virus

<400> SEQUENCE: 17
aaagaattca tgagtcttct aaccgaggtc gaaacgta 38

<210> SEQ ID NO 18
<211> LENGTH: 38
<212> TYPE: DNA
<213> ORGANISM: Influenza virus

<400> SEQUENCE: 18
aaattcgaat tactccagct ctatgctgac aaaatgac 38

<210> SEQ ID NO 19
<211> LENGTH: 57
<212> TYPE: DNA
<213> ORGANISM: Influenza virus

<400> SEQUENCE: 19
agaatcatga gtcttctaac cgaggtcgaa acgcctatca gaaacgaatg gggtgc 57

<210> SEQ ID NO 20
<211> LENGTH: 38
<212> TYPE: DNA
<213> ORGANISM: Influenza virus

<400> SEQUENCE: 20
aaattcgaat tactccagct ctatgctgac aaaatgac 38

<210> SEQ ID NO 21
<211> LENGTH: 30
<212> TYPE: DNA
<213> ORGANISM: Influenza virus

<400> SEQUENCE: 21
agaattcatg gcgtcccaag gcaccaaacg 30

<210> SEQ ID NO 22
<211> LENGTH: 50
<212> TYPE: DNA
<213> ORGANISM: Influenza virus

<400> SEQUENCE: 22
agcggccgct taattgtcgt actcctctgc attgtctccg aagaaataag 50

<210> SEQ ID NO 23
<211> LENGTH: 35
<212> TYPE: DNA
<213> ORGANISM: Influenza virus

<400> SEQUENCE: 23
agaattcatg aaggcaataa ttgtactact catgg 35

<210> SEQ ID NO 24
<211> LENGTH: 47
<212> TYPE: DNA
<213> ORGANISM: Influenza virus

<400> SEQUENCE: 24
agcggccgct tatagacaga tggagcaaga aacattgtct ctggaga 47

<210> SEQ ID NO 25
<211> LENGTH: 31
<212> TYPE: DNA
<213> ORGANISM: Influenza virus

<400> SEQUENCE: 25
agaattcatg ctaccttcaa ctatacaaac g 31

<210> SEQ ID NO 26
<211> LENGTH: 40
<212> TYPE: DNA
<213> ORGANISM: Influenza virus

<400> SEQUENCE: 26
agcggccgct tacagagcca tatcaacacc tgtgacagtg 40

<210> SEQ ID NO 27
<211> LENGTH: 568
<212> TYPE: PRT
<213> ORGANISM: Unknown
<220> FEATURE:
<223> OTHER INFORMATION: Vac2-hac-opt

<400> SEQUENCE: 27

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240
```

```
Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565
```

```
<210> SEQ ID NO 28
<211> LENGTH: 572
<212> TYPE: PRT
<213> ORGANISM: Unknown
<220> FEATURE:
<223> OTHER INFORMATION: Vac2-hac-spc-opt

<400> SEQUENCE: 28

Met Pro Leu Tyr Lys Leu Leu Asn Val Leu Trp Leu Val Ala Val Ser
1               5                   10                  15

Asn Ala Ile Pro Asp Gln Ile Cys Ile Gly Tyr His Ala Asn Asn Ser
            20                  25                  30
```

-continued

```
Thr Glu Gln Val Asp Thr Ile Met Glu Lys Asn Val Thr Val Thr His
        35                  40                  45

Ala Gln Asp Ile Leu Glu Lys Thr His Asn Gly Lys Leu Cys Asp Leu
    50                  55                  60

Asp Gly Val Lys Pro Leu Ile Leu Arg Asp Cys Ser Val Ala Gly Trp
65                  70                  75                  80

Leu Leu Gly Asn Pro Met Cys Asp Glu Phe Ile Asn Val Pro Glu Trp
                85                  90                  95

Ser Tyr Ile Val Glu Lys Ala Asn Pro Thr Asn Asp Leu Cys Tyr Pro
            100                 105                 110

Gly Ser Phe Asn Asp Tyr Glu Glu Leu Lys His Leu Leu Ser Arg Ile
        115                 120                 125

Asn His Phe Glu Lys Ile Gln Ile Ile Pro Lys Ser Ser Trp Ser Asp
    130                 135                 140

His Glu Ala Ser Ser Gly Val Ser Ser Ala Cys Pro Tyr Leu Gly Ser
145                 150                 155                 160

Pro Ser Phe Phe Arg Asn Val Val Trp Leu Ile Lys Lys Asn Ser Thr
                165                 170                 175

Tyr Pro Thr Ile Lys Lys Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Arg Leu Tyr Gln Asn Pro Thr Thr Tyr Ile Ser Ile Gly Thr Ser Thr
    210                 215                 220

Leu Asn Gln Arg Leu Val Pro Lys Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

Ala Tyr Lys Ile Val Lys Lys Gly Asp Ser Ala Ile Met Lys Ser Glu
        275                 280                 285

Leu Glu Tyr Gly Asn Cys Asn Thr Lys Cys Gln Thr Pro Met Gly Ala
    290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Ser Arg Arg Lys Lys Arg Gly Leu
            340                 345                 350

Phe Gly Ala Ile Ala Gly Phe Ile Glu Gly Gly Trp Gln Gly Met Val
        355                 360                 365

Asp Gly Trp Tyr Gly Tyr His His Ser Asn Glu Gln Gly Ser Gly Tyr
    370                 375                 380

Ala Ala Asp Lys Glu Ser Thr Gln Lys Ala Ile Asp Gly Val Thr Asn
385                 390                 395                 400

Lys Val Asn Ser Ile Ile Asp Lys Met Asn Thr Gln Phe Glu Ala Val
                405                 410                 415

Gly Arg Glu Phe Asn Asn Leu Glu Arg Arg Ile Glu Asn Leu Asn Lys
            420                 425                 430

Lys Met Glu Asp Gly Phe Leu Asp Val Trp Thr Tyr Asn Ala Glu Leu
        435                 440                 445

Leu Val Leu Met Glu Asn Glu Arg Thr Leu Asp Phe His Asp Ser Asn
```

```
    450                 455                 460

Val Lys Asn Leu Tyr Asp Lys Val Arg Leu Gln Leu Arg Asp Asn Ala
465                 470                 475                 480

Lys Glu Leu Gly Asn Gly Cys Phe Glu Phe Tyr His Lys Cys Asp Asn
                485                 490                 495

Glu Cys Met Glu Ser Ile Arg Asn Gly Thr Tyr Asn Tyr Pro Gln Tyr
            500                 505                 510

Ser Glu Glu Ala Arg Leu Lys Arg Glu Glu Ile Ser Gly Val Lys Leu
        515                 520                 525

Glu Ser Ile Gly Thr Tyr Gln Ile Leu Ser Ile Tyr Ser Thr Val Ala
    530                 535                 540

Ser Ser Leu Ala Leu Ala Ile Met Met Ala Gly Leu Ser Leu Trp Met
545                 550                 555                 560

Cys Ser Asn Gly Ser Leu Gln Cys Arg Ile Cys Ile
                565                 570


<210> SEQ ID NO 29
<211> LENGTH: 570
<212> TYPE: PRT
<213> ORGANISM: Unknown
<220> FEATURE:
<223> OTHER INFORMATION: Vac2-hac-sph9-opt

<400> SEQUENCE: 29

Met Glu Thr Ile Ser Leu Ile Thr Ile Leu Leu Val Val Thr Ala Ser
1               5                   10                  15

Asn Ala Asp Gln Ile Cys Ile Gly Tyr His Ala Asn Asn Ser Thr Glu
            20                  25                  30

Gln Val Asp Thr Ile Met Glu Lys Asn Val Thr Val Thr His Ala Gln
        35                  40                  45

Asp Ile Leu Glu Lys Thr His Asn Gly Lys Leu Cys Asp Leu Asp Gly
    50                  55                  60

Val Lys Pro Leu Ile Leu Arg Asp Cys Ser Val Ala Gly Trp Leu Leu
65                  70                  75                  80

Gly Asn Pro Met Cys Asp Glu Phe Ile Asn Val Pro Glu Trp Ser Tyr
                85                  90                  95

Ile Val Glu Lys Ala Asn Pro Thr Asn Asp Leu Cys Tyr Pro Gly Ser
            100                 105                 110

Phe Asn Asp Tyr Glu Glu Leu Lys His Leu Leu Ser Arg Ile Asn His
        115                 120                 125

Phe Glu Lys Ile Gln Ile Ile Pro Lys Ser Ser Trp Ser Asp His Glu
    130                 135                 140

Ala Ser Ser Gly Val Ser Ser Ala Cys Pro Tyr Leu Gly Ser Pro Ser
145                 150                 155                 160

Phe Phe Arg Asn Val Val Trp Leu Ile Lys Lys Asn Ser Thr Tyr Pro
                165                 170                 175

Thr Ile Lys Lys Ser Tyr Asn Asn Thr Asn Gln Glu Asp Leu Leu Val
            180                 185                 190

Leu Trp Gly Ile His His Pro Asn Asp Ala Ala Glu Gln Thr Arg Leu
        195                 200                 205

Tyr Gln Asn Pro Thr Thr Tyr Ile Ser Ile Gly Thr Ser Thr Leu Asn
    210                 215                 220

Gln Arg Leu Val Pro Lys Ile Ala Thr Arg Ser Lys Val Asn Gly Gln
225                 230                 235                 240

Ser Gly Arg Met Glu Phe Phe Trp Thr Ile Leu Lys Pro Asn Asp Ala
```

```
                245                 250                 255

Ile Asn Phe Glu Ser Asn Gly Asn Phe Ile Ala Pro Glu Tyr Ala Tyr
            260                 265                 270

Lys Ile Val Lys Lys Gly Asp Ser Ala Ile Met Lys Ser Glu Leu Glu
        275                 280                 285

Tyr Gly Asn Cys Asn Thr Lys Cys Gln Thr Pro Met Gly Ala Ile Asn
    290                 295                 300

Ser Ser Met Pro Phe His Asn Ile His Pro Leu Thr Ile Gly Glu Cys
305                 310                 315                 320

Pro Lys Tyr Val Lys Ser Asn Arg Leu Val Leu Ala Thr Gly Leu Arg
                325                 330                 335

Asn Ser Pro Gln Arg Glu Ser Arg Arg Lys Lys Arg Gly Leu Phe Gly
            340                 345                 350

Ala Ile Ala Gly Phe Ile Glu Gly Gly Trp Gln Gly Met Val Asp Gly
        355                 360                 365

Trp Tyr Gly Tyr His His Ser Asn Glu Gln Gly Ser Gly Tyr Ala Ala
    370                 375                 380

Asp Lys Glu Ser Thr Gln Lys Ala Ile Asp Gly Val Thr Asn Lys Val
385                 390                 395                 400

Asn Ser Ile Ile Asp Lys Met Asn Thr Gln Phe Glu Ala Val Gly Arg
                405                 410                 415

Glu Phe Asn Asn Leu Glu Arg Arg Ile Glu Asn Leu Asn Lys Lys Met
            420                 425                 430

Glu Asp Gly Phe Leu Asp Val Trp Thr Tyr Asn Ala Glu Leu Leu Val
        435                 440                 445

Leu Met Glu Asn Glu Arg Thr Leu Asp Phe His Asp Ser Asn Val Lys
    450                 455                 460

Asn Leu Tyr Asp Lys Val Arg Leu Gln Leu Arg Asp Asn Ala Lys Glu
465                 470                 475                 480

Leu Gly Asn Gly Cys Phe Glu Phe Tyr His Lys Cys Asp Asn Glu Cys
                485                 490                 495

Met Glu Ser Ile Arg Asn Gly Thr Tyr Asn Tyr Pro Gln Tyr Ser Glu
            500                 505                 510

Glu Ala Arg Leu Lys Arg Glu Glu Ile Ser Gly Val Lys Leu Glu Ser
        515                 520                 525

Ile Gly Thr Tyr Gln Ile Leu Ser Ile Tyr Ser Thr Val Ala Ser Ser
    530                 535                 540

Leu Ala Leu Ala Ile Met Met Ala Gly Leu Ser Leu Trp Met Cys Ser
545                 550                 555                 560

Asn Gly Ser Leu Gln Cys Arg Ile Cys Ile
                565                 570


<210> SEQ ID NO 30
<211> LENGTH: 564
<212> TYPE: PRT
<213> ORGANISM: Unknown
<220> FEATURE:
<223> OTHER INFORMATION: Vac2-hac-cs-opt

<400> SEQUENCE: 30

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
```

-continued

```
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460
```

```
Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Ile Arg Asn
                485                 490                 495

Gly Thr Tyr Asn Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
    530                 535                 540

Met Ala Gly Leu Ser Leu Trp Met Cys Ser Asn Gly Ser Leu Gln Cys
545                 550                 555                 560

Arg Ile Cys Ile


<210> SEQ ID NO 31
<211> LENGTH: 449
<212> TYPE: PRT
<213> ORGANISM: Unknown
<220> FEATURE:
<223> OTHER INFORMATION: Vac2-naj-opt

<400> SEQUENCE: 31

Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ile
            20                  25                  30

Trp Val Ser His Ser Ile Gln Thr Gly Asn Gln His Gln Ala Glu Ser
        35                  40                  45

Ile Ser Asn Thr Asn Pro Leu Thr Glu Lys Ala Val Ala Ser Val Thr
    50                  55                  60

Leu Ala Gly Asn Ser Ser Leu Cys Pro Ile Arg Gly Trp Ala Val His
65                  70                  75                  80

Ser Lys Asp Asn Asn Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Glu Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asp Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255
```

Glu Glu Cys Ser Cys Tyr Pro Asp Ala Gly Glu Ile Thr Cys Val Cys
260 265 270

Arg Asp Asn Trp His Gly Ser Asn Arg Pro Trp Val Ser Phe Asn Gln
275 280 285

Asn Leu Glu Tyr Gln Ile Gly Tyr Ile Cys Ser Gly Val Phe Gly Asp
290 295 300

Asn Pro Arg Pro Asn Asp Gly Thr Gly Ser Cys Gly Pro Met Ser Pro
305 310 315 320

Asn Gly Ala Tyr Gly Val Lys Gly Phe Ser Phe Lys Tyr Gly Asn Gly
325 330 335

Val Trp Ile Gly Arg Thr Lys Ser Thr Asn Ser Arg Ser Gly Phe Glu
340 345 350

Met Ile Trp Asp Pro Asn Gly Trp Thr Gly Thr Asp Ser Ser Phe Ser
355 360 365

Val Lys Gln Asp Ile Val Ala Ile Thr Asp Trp Ser Gly Tyr Ser Gly
370 375 380

Ser Phe Val Gln His Pro Glu Leu Thr Gly Leu Asp Cys Ile Arg Pro
385 390 395 400

Cys Phe Trp Val Glu Leu Ile Arg Gly Arg Pro Lys Glu Ser Thr Ile
405 410 415

Trp Thr Ser Gly Ser Ser Ile Ser Phe Cys Gly Val Asn Ser Asp Thr
420 425 430

Val Ser Trp Ser Trp Pro Asp Gly Ala Glu Leu Pro Phe Thr Ile Asp
435 440 445

Lys

<210> SEQ ID NO 32
<211> LENGTH: 252
<212> TYPE: PRT
<213> ORGANISM: Unknown
<220> FEATURE:
<223> OTHER INFORMATION: Vac2-mc-opt

<400> SEQUENCE: 32

Met Ser Leu Leu Thr Glu Val Glu Thr Tyr Val Leu Ser Ile Ile Pro
1 5 10 15

Ser Gly Pro Leu Lys Ala Glu Ile Ala Gln Lys Leu Glu Asp Val Phe
20 25 30

Ala Gly Lys Asn Thr Asp Leu Glu Ala Leu Met Glu Trp Leu Lys Thr
35 40 45

Arg Pro Ile Leu Ser Pro Leu Thr Lys Gly Ile Leu Gly Phe Val Phe
50 55 60

Thr Leu Thr Val Pro Ser Glu Arg Gly Leu Gln Arg Arg Arg Phe Val
65 70 75 80

Gln Asn Ala Leu Asn Gly Asn Gly Asp Pro Asn Asn Met Asp Arg Ala
85 90 95

Val Lys Leu Tyr Lys Lys Leu Lys Arg Glu Ile Thr Phe His Gly Ala
100 105 110

Lys Glu Val Ser Leu Ser Tyr Ser Thr Gly Ala Leu Ala Ser Cys Met
115 120 125

Gly Leu Ile Tyr Asn Arg Met Gly Thr Val Thr Thr Glu Val Ala Phe
130 135 140

Gly Leu Val Cys Ala Thr Cys Glu Gln Ile Ala Asp Ser Gln His Arg
145 150 155 160

Ser His Arg Gln Met Ala Thr Ile Thr Asn Pro Leu Ile Arg His Glu

```
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Asn Gln
        195                 200                 205

Ala Arg Gln Met Val Gln Ala Met Arg Thr Ile Gly Thr His Pro Asn
    210                 215                 220

Ser Ser Ala Gly Leu Arg Asp Asn Leu Leu Glu Asn Leu Gln Ala Tyr
225                 230                 235                 240

Gln Lys Arg Met Gly Val Gln Met Gln Arg Phe Lys
                245                 250


<210> SEQ ID NO 33
<211> LENGTH: 564
<212> TYPE: PRT
<213> ORGANISM: Unknown
<220> FEATURE:
<223> OTHER INFORMATION: VN1203-ha-cs-opt

<400> SEQUENCE: 33

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Asn Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Asn Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
```

-continued

```
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile


<210> SEQ ID NO 34
<211> LENGTH: 572
<212> TYPE: PRT
<213> ORGANISM: Unknown
<220> FEATURE:
<223> OTHER INFORMATION: VN1203-ha-spc-opt

<400> SEQUENCE: 34

Met Pro Leu Tyr Lys Leu Leu Asn Val Leu Trp Leu Val Ala Val Ser
1               5                   10                  15

Asn Ala Ile Pro Asp Gln Ile Cys Ile Gly Tyr His Ala Asn Asn Ser
            20                  25                  30

Thr Glu Gln Val Asp Thr Ile Met Glu Lys Asn Val Thr Val Thr His
        35                  40                  45

Ala Gln Asp Ile Leu Glu Lys Thr His Asn Gly Lys Leu Cys Asp Leu
    50                  55                  60

Asp Gly Val Lys Pro Leu Ile Leu Arg Asp Cys Ser Val Ala Gly Trp
65                  70                  75                  80
```

```
Leu Leu Gly Asn Pro Met Cys Asp Glu Phe Ile Asn Val Pro Glu Trp
                85                  90                  95

Ser Tyr Ile Val Glu Lys Ala Asn Pro Ala Asn Asp Leu Cys Tyr Pro
            100                 105                 110

Gly Asp Phe Asn Asp Tyr Glu Glu Leu Lys His Leu Leu Ser Arg Ile
        115                 120                 125

Asn His Phe Glu Lys Ile Gln Ile Ile Pro Lys Asn Ser Trp Ser Ser
    130                 135                 140

His Glu Ala Ser Leu Gly Val Ser Ser Ala Cys Pro Tyr Gln Gly Lys
145                 150                 155                 160

Ser Ser Phe Phe Arg Asn Val Val Trp Leu Ile Lys Lys Asn Asn Ala
                165                 170                 175

Tyr Pro Thr Ile Lys Arg Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Arg Leu Tyr Gln Asn Pro Thr Thr Tyr Ile Ser Val Gly Thr Ser Thr
    210                 215                 220

Leu Asn Gln Arg Leu Val Pro Lys Ile Ala Thr Arg Ser Lys Val Asn
225                 230                 235                 240

Gly Gln Asn Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

Ala Tyr Lys Ile Val Lys Lys Gly Asp Ser Ala Ile Met Lys Ser Glu
        275                 280                 285

Leu Glu Tyr Gly Asn Cys Asn Thr Lys Cys Gln Thr Pro Met Gly Ala
    290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Arg Arg Arg Lys Lys Arg Gly Leu
            340                 345                 350

Phe Gly Ala Ile Ala Gly Phe Ile Glu Gly Gly Trp Gln Gly Met Val
        355                 360                 365

Asp Gly Trp Tyr Gly Tyr His His Ser Asn Glu Gln Gly Ser Gly Tyr
    370                 375                 380

Ala Ala Asp Lys Glu Ser Thr Gln Lys Ala Ile Asp Gly Val Thr Asn
385                 390                 395                 400

Lys Val Asn Ser Ile Ile Asp Lys Met Asn Thr Gln Phe Glu Ala Val
                405                 410                 415

Gly Arg Glu Phe Asn Asn Leu Glu Arg Arg Ile Glu Asn Leu Asn Lys
            420                 425                 430

Lys Met Glu Asp Gly Phe Leu Asp Val Trp Thr Tyr Asn Ala Glu Leu
        435                 440                 445

Leu Val Leu Met Glu Asn Glu Arg Thr Leu Asp Phe His Asp Ser Asn
    450                 455                 460

Val Lys Asn Leu Tyr Asp Lys Val Arg Leu Gln Leu Arg Asp Asn Ala
465                 470                 475                 480

Lys Glu Leu Gly Asn Gly Cys Phe Glu Phe Tyr His Lys Cys Asp Asn
                485                 490                 495
```

```
Glu Cys Met Glu Ser Val Arg Asn Gly Thr Tyr Asp Tyr Pro Gln Tyr
            500                 505                 510

Ser Glu Glu Ala Arg Leu Lys Arg Glu Glu Ile Ser Gly Val Lys Leu
        515                 520                 525

Glu Ser Ile Gly Thr Tyr Gln Ile Leu Ser Ile Tyr Ser Thr Val Ala
    530                 535                 540

Ser Ser Leu Ala Leu Ala Ile Met Val Ala Gly Leu Ser Leu Trp Met
545                 550                 555                 560

Cys Ser Asn Gly Ser Leu Gln Cys Arg Ile Cys Ile
                565                 570


<210> SEQ ID NO 35
<211> LENGTH: 570
<212> TYPE: PRT
<213> ORGANISM: Unknown
<220> FEATURE:
<223> OTHER INFORMATION: VN1203-ha-sph9-opt

<400> SEQUENCE: 35

Met Glu Thr Ile Ser Leu Ile Thr Ile Leu Leu Val Val Thr Ala Ser
1               5                   10                  15

Asn Ala Asp Gln Ile Cys Ile Gly Tyr His Ala Asn Asn Ser Thr Glu
            20                  25                  30

Gln Val Asp Thr Ile Met Glu Lys Asn Val Thr Val Thr His Ala Gln
        35                  40                  45

Asp Ile Leu Glu Lys Thr His Asn Gly Lys Leu Cys Asp Leu Asp Gly
    50                  55                  60

Val Lys Pro Leu Ile Leu Arg Asp Cys Ser Val Ala Gly Trp Leu Leu
65                  70                  75                  80

Gly Asn Pro Met Cys Asp Glu Phe Ile Asn Val Pro Glu Trp Ser Tyr
                85                  90                  95

Ile Val Glu Lys Ala Asn Pro Ala Asn Asp Leu Cys Tyr Pro Gly Asp
            100                 105                 110

Phe Asn Asp Tyr Glu Glu Leu Lys His Leu Leu Ser Arg Ile Asn His
        115                 120                 125

Phe Glu Lys Ile Gln Ile Ile Pro Lys Asn Ser Trp Ser Ser His Glu
    130                 135                 140

Ala Ser Leu Gly Val Ser Ser Ala Cys Pro Tyr Gln Gly Lys Ser Ser
145                 150                 155                 160

Phe Phe Arg Asn Val Val Trp Leu Ile Lys Lys Asn Asn Ala Tyr Pro
                165                 170                 175

Thr Ile Lys Arg Ser Tyr Asn Asn Thr Asn Gln Glu Asp Leu Leu Val
            180                 185                 190

Leu Trp Gly Ile His His Pro Asn Asp Ala Ala Glu Gln Thr Arg Leu
        195                 200                 205

Tyr Gln Asn Pro Thr Thr Tyr Ile Ser Val Gly Thr Ser Thr Leu Asn
    210                 215                 220

Gln Arg Leu Val Pro Lys Ile Ala Thr Arg Ser Lys Val Asn Gly Gln
225                 230                 235                 240

Asn Gly Arg Met Glu Phe Phe Trp Thr Ile Leu Lys Pro Asn Asp Ala
                245                 250                 255

Ile Asn Phe Glu Ser Asn Gly Asn Phe Ile Ala Pro Glu Tyr Ala Tyr
            260                 265                 270

Lys Ile Val Lys Lys Gly Asp Ser Ala Ile Met Lys Ser Glu Leu Glu
        275                 280                 285
```

-continued

```
Tyr Gly Asn Cys Asn Thr Lys Cys Gln Thr Pro Met Gly Ala Ile Asn
    290                 295                 300

Ser Ser Met Pro Phe His Asn Ile His Pro Leu Thr Ile Gly Glu Cys
305                 310                 315                 320

Pro Lys Tyr Val Lys Ser Asn Arg Leu Val Leu Ala Thr Gly Leu Arg
                325                 330                 335

Asn Ser Pro Gln Arg Glu Arg Arg Arg Lys Lys Arg Gly Leu Phe Gly
            340                 345                 350

Ala Ile Ala Gly Phe Ile Glu Gly Gly Trp Gln Gly Met Val Asp Gly
        355                 360                 365

Trp Tyr Gly Tyr His His Ser Asn Glu Gln Gly Ser Gly Tyr Ala Ala
    370                 375                 380

Asp Lys Glu Ser Thr Gln Lys Ala Ile Asp Gly Val Thr Asn Lys Val
385                 390                 395                 400

Asn Ser Ile Ile Asp Lys Met Asn Thr Gln Phe Glu Ala Val Gly Arg
                405                 410                 415

Glu Phe Asn Asn Leu Glu Arg Arg Ile Glu Asn Leu Asn Lys Lys Met
            420                 425                 430

Glu Asp Gly Phe Leu Asp Val Trp Thr Tyr Asn Ala Glu Leu Leu Val
        435                 440                 445

Leu Met Glu Asn Glu Arg Thr Leu Asp Phe His Asp Ser Asn Val Lys
    450                 455                 460

Asn Leu Tyr Asp Lys Val Arg Leu Gln Leu Arg Asp Asn Ala Lys Glu
465                 470                 475                 480

Leu Gly Asn Gly Cys Phe Glu Phe Tyr His Lys Cys Asp Asn Glu Cys
                485                 490                 495

Met Glu Ser Val Arg Asn Gly Thr Tyr Asp Tyr Pro Gln Tyr Ser Glu
            500                 505                 510

Glu Ala Arg Leu Lys Arg Glu Glu Ile Ser Gly Val Lys Leu Glu Ser
        515                 520                 525

Ile Gly Thr Tyr Gln Ile Leu Ser Ile Tyr Ser Thr Val Ala Ser Ser
    530                 535                 540

Leu Ala Leu Ala Ile Met Val Ala Gly Leu Ser Leu Trp Met Cys Ser
545                 550                 555                 560

Asn Gly Ser Leu Gln Cys Arg Ile Cys Ile
                565                 570


<210> SEQ ID NO 36
<211> LENGTH: 1707
<212> TYPE: DNA
<213> ORGANISM: Influenza virus

<400> SEQUENCE: 36

atggagaaaa tagtgcttct ttttgcaata gtcagtcttg ttaaaagtga tcagatttgc     60

attggttacc atgcaaacaa ctcgacagag caggttgaca caataatgga aaagaacgtt    120

actgttacac atgcccaaga catactggaa aagaaacaca acgggaagct ctgcgatcta    180

gatggagtga agcctctaat tttgagagat tgtagcgtag ctggatggct cctcggaaac    240

ccaatgtgtg acgaattcat caatgtgccg gaatggtctt acatagtgga gaaggccaat    300

ccagtcaatg acctctgtta cccaggggat ttcaatgact atgaagaatt gaaacaccta    360

ttgagcagaa taaaccattt tgagaaaatt cagatcatcc ccaaaagttc ttggtccagt    420

catgaagcct cattaggggt gagctcagca tgtccatacc agggaaagtc ctcctttttc    480

agaaatgtgg tatggcttat caaaaagaac agtacatacc caacaataaa gaggagctac    540
```

```
aataatacca accaagaaga tcttttggta ctgtggggga ttcaccatcc taatgatgcg    600

gcagagcaga caaagctcta tcaaaaccca accacctata tttccgttgg gacatcaaca    660

ctaaaccaga gattggtacc aagaatagct actagatcca aagtaaacgg gcaaagtgga    720

aggatggagt tcttctggac aattttaaag ccgaatgatg caatcaactt cgagagtaat    780

ggaaatttca ttgctccaga atatgcatac aaaattgtca agaaagggga ctcaacaatt    840

atgaaaagtg aattggaata tggtaactgc aacaccaagt gtcaaactcc aatgggggcg    900

ataaactcta gcatgccatt ccacaatata caccctctca ccattgggga atgccccaaa    960

tatgtgaaat caaacagatt agtccttgcg actgggctca gaaatagccc tcaaagagag   1020

agaagaagaa aaaagagagg attatttgga gctatagcag gttttataga gggaggatgg   1080

cagggaatgg tagatggttg gtatgggtac caccatagca atgagcaggg gagtgggtac   1140

gctgcagaca aagaatccac tcaaaaggca atagatggag tcaccaataa ggtcaactcg   1200

atcattgaca aaatgaacac tcagtttgag gccgttggaa gggaatttaa caacttagaa   1260

aggagaatag agaatttaaa caagaagatg gaagacgggt tcctagatgt ctggacttat   1320

aatgctgaac ttctggttct catggaaaat gagagaactc tagactttca tgactcaaat   1380

gtcaagaacc tttacgacaa ggtccgacta cagcttaggg ataatgcaaa ggagctgggt   1440

aacggttgtt tcgagttcta tcataaatgt gataatgaat gtatggaaag tgtaagaaat   1500

ggaacgtatg actacccgca gtattcagaa gaagcgagac taaaaagaga ggaaataagt   1560

ggagtaaaat tggaatcaat aggaatttac caaatactgt caatttattc tacagtggcg   1620

agttccctag cactggcaat catggtagct ggtctatcct tatggatgtg ctccaatgga   1680

tcgttacaat gcagaatttg catttaa                                       1707
```

```
<210> SEQ ID NO 37
<211> LENGTH: 1750
<212> TYPE: DNA
<213> ORGANISM: Influenza virus

<400> SEQUENCE: 37

agtgtgatgg atatctgcag aattcgccct taggcgcgcc atggagaaaa tagtgcttct     60

ttttgcaata gtcagtcttg ttaaaagtga tcagatttgc attggttacc atgcaaacaa    120

ctcgacagag caggttgaca caataatgga aaagaacgtt actgttacac atgcccaaga    180

catactggaa aagaaacaca acgggaagct ctgcgatcta gatggagtga agcctctaat    240

tttgagagat tgtagcgtag ctggatggct cctcggaaac ccaatgtgtg acgaattcat    300

caatgtgccg gaatggtctt acatagtgga gaaggccaat ccagtcaatg acctctgtta    360

cccaggggat ttcaatgact atgaagaatt gaaacaccta ttgagcagaa taaaccattt    420

tgagaaaatt cagatcatcc ccaaaagttc ttggtccagt catgaagcct cattaggggt    480

gagctcagca tgtccatacc agggaaagtc ctccttttc agaaatgtgg tatggcttat     540

caaaaagaac agtacatacc caacaataaa gaggagctac aataatacca accaagaaga    600

tcttttggta ctgtggggga ttcaccatcc taatgatgcg gcagagcaga caaagctcta    660

tcaaaaccca accacctata tttccgttgg gacatcaaca ctaaaccaga gattggtacc    720

aagaatagct actagatcca aagtaaacgg gcaaagtgga aggatggagt tcttctggac    780

aattttaaag ccgaatgatg caatcaactt cgagagtaat ggaaatttca ttgctccaga    840

atatgcatac aaaattgtca agaaagggga ctcaacaatt atgaaaagtg aattggaata    900
```

```
tggtaactgc aacaccaagt gtcaaactcc aatgggggcg ataaactcta gcatgccatt    960

ccacaatata caccctctca ccattgggga atgccccaaa tatgtgaaat caaacagatt   1020

agtccttgcg actgggctca gaaatagccc tcaaagagag agaagaagaa aaaagagagg   1080

attatttgga gctatagcag gttttataga gggaggatgg cagggaatgg tagatggttg   1140

gtatgggtac caccatagca atgagcaggg gagtgggtac gctgcagaca aagaatccac   1200

tcaaaaggca atagatggag tcaccaataa ggtcaactcg atcattgaca aaatgaacac   1260

tcagtttgag gccgttggaa gggaatttaa caacttagaa aggagaatag agaatttaaa   1320

caagaagatg gaagacgggt tcctagatgt ctggacttat aatgctgaac ttctggttct   1380

catggaaaat gagagaactc tagactttca tgactcaaat gtcaagaacc tttacgacaa   1440

ggtccgacta cagcttaggg ataatgcaaa ggagctgggt aacggttgtt tcgagttcta   1500

tcataaatgt gataatgaat gtatggaaag tgtaagaaat ggaacgtatg actacccgca   1560

gtattcagaa gaagcgagac taaaaagaga ggaaataagt ggagtaaaat tggaatcaat   1620

aggaatttac caaatactgt caatttattc tacagtggcg agttccctag cactggcaat   1680

catggtagct ggtctatcct tatggatgtg ctccaatggg tcgttacaat gcagaatttg   1740

catttaagcg                                                          1750
```

```
<210> SEQ ID NO 38
<211> LENGTH: 1350
<212> TYPE: DNA
<213> ORGANISM: Influenza virus

<400> SEQUENCE: 38

atgaatccaa atcagaagat aataaccatc ggatcaatct gtatggtaac tggaatagtt     60

agcttaatgt tacaaattgg gaacatgatc tcaatatggg tcagtcattc aattcacaca    120

gggaatcaac accaatctga accaatcagc aatactaatt ttcttactga gaaagctgtg    180

gcttcagtaa aattagcggg caattcatct ctttgcccca ttaacggatg ggctgtatac    240

agtaaggaca acagtataag gatcggttcc aagggggatg tgtttgttat aagagagccg    300

ttcatctcat gctcccactt ggaatgcaga actttctttt tgactcaggg agccttgctg    360

aatgacaagc actccaatgg gactgtcaaa gacagaagcc ctcacagaac attaatgagt    420

tgtcctgtgg gtgaggctcc ctccccatat aactcaaggt ttgagtctgt tgcttggtca    480

gcaagtgctt gccatgatgg caccagttgg ttgacgattg gaatttctgg cccagacaat    540

ggggctgtgg ctgtattgaa atacaatggc ataataacag acactatcaa gagttggagg    600

aacaacatac tgagaactca agagtctgaa tgtgcatgtg taaatggctc ttgctttact    660

gtaatgactg acggaccaag taatggtcag gcatcacata agatcttcaa aatggaaaaa    720

gggaaagtgg ttaaatcagt cgaattggat gctcctaatt atcactatga ggaatgctcc    780

tgttatccta atgccggaga aatcacatgt gtgtgcaggg ataattggca tggctcaaat    840

cggccatggg tatctttcaa tcaaaatttg gagtatcaaa taggatatat atgcagtgga    900

gttttcggag acaatccacg ccccaatgat ggaacaggta gttgtggtcc ggtgtcctct    960

aacggggcat atggggtaaa agggttttca tttaaatacg gcaatggtgt ctggatcggg   1020

agaaccaaaa gcactaattc caggagcggc tttgaaatga tttgggatcc aaatgggtgg   1080

actgaaacgg acagtagctt ttcagtgaaa caagatatcg tagcaataac tgattggtca   1140

ggatatagcg ggagttttgt ccagcatcca gaactgacag gactagattg cataagacct   1200

tgtttctggg ttgagttgat cagagggcgg cccaaagaga gcacaatttg gactagtggg   1260
```

```
agcagcatat ctttttgtgg tgtaaatagt gacactgtgg gttggtcttg gccagacggt   1320

gccgagttgc cattcaccat tgacaagtag                                     1350
```

<210> SEQ ID NO 39
<211> LENGTH: 1400
<212> TYPE: DNA
<213> ORGANISM: Influenza virus

<400> SEQUENCE: 39

```
ccgggatgaa tccaaatcag aagataataa ccatcggatc aatctgtatg gtaactggaa     60

tagttagctt aatgttacaa attgggaaca tgatctcaat atgggtcagt cattcaattc    120

acacagggaa tcaacaccaa tctgaaccaa tcagcaatac taattttctt actgagaaag    180

ctgtggcttc agtaaaatta gcgggcaatt catctctttg ccccattaac ggatgggctg    240

tatacagtaa ggacaacagt ataaggatcg gttccaaggg ggatgtgttt gttataagag    300

agccgttcat ctcatgctcc cacttggaat gcagaacttt ctttttgact cagggagcct    360

cgctgaatga caagcactcc aatgggactg tcaaagacag aagccctcac agaacattaa    420

tgagttgtcc tgtgggtgag gctccctccc catataactc aaggtttgag tctgttgctt    480

ggtcagcaag tgcttgccat gatggcacca gttggttgac gattggaatt tctggcccag    540

acaatggggc tgtggctgta ttgaaataca atggcataat aacagacact atcaagagtt    600

ggaggaacaa catactgaga actcaagagt ctgaatgtgc atgtgtaaat ggctcttgct    660

ttactgtaat gactgacgga ccaagtaatg gtcaggcatc acataagatc ttcaaaatgg    720

aaaaagggaa agtggttaaa tcagtcgaat tggatgctcc taattatcac tatgaggaat    780

gctcctgtta tcctaatgcc ggagaaatca catgtgtgtg cagggataat tggcatggct    840

caaatcggcc atgggtatct ttcaatcaaa atttggagta tcaaatagga tatatatgca    900

gtggagtttt cggagacaat ccacgcccca atgatggaac aggtagttgt ggtccggtgt    960

cctctaacgg ggcatatggg gtaaaagggt tttcatttaa atacggcaat ggtgtctgga   1020

tcgggagaac caaaagcact aattccagga gcggctttga aatgatttgg gatccaaatg   1080

ggtggactga aacggacagt agcttttcag tgaaacaaga tatcgtagca ataactgatt   1140

ggtcaggata tagcgggagt tttgtccagc atccagaact gacaggacta gattgcataa   1200

gaccttgttt ctgggttgag ttgatcagag ggcggcccaa agagagcaca atttggacta   1260

gtgggagcag catatctttt tgtggtgtaa atagtgacac tgtgggttgg tcttggccag   1320

acggtgctga gttgccattc accattgaca agtaggggcc ctcgagtaag ggcgaattcc   1380

agcacactgg cggccgttac                                                1400
```

<210> SEQ ID NO 40
<211> LENGTH: 759
<212> TYPE: DNA
<213> ORGANISM: Influenza virus

<400> SEQUENCE: 40

```
atgagtcttc taaccgaggt cgaaacgtac gttctctcta tcatcccgtc aggccccctc     60

aaagccgaga tcgcacagaa acttgaagat gtctttgcag gaaagaacac cgatctcgag    120

gctctcatgg agtggctaaa gacaagacca atcctgtcac ctctgactaa agggattttg    180

ggatttgtat tcacgctcac cgtgcccagt gagcgaggac tgcagcgtag acgctttgtc    240

cagaatgccc taaatggaaa tggagatcca aataatatgg atagggcagt taagctatat    300
```

-continued aagaagctga aaagagaaat aacattccat ggggctaagg aggtcgcact cagctactca 360
accggtgcac ttgccagttg catgggtctc atatacaaca ggatgggaac ggtgactacg 420
gaagtggctt ttggcctagt gtgtgccact tgtgagcaga ttgcagattc acagcatcgg 480
tctcacagac agatggcaac tatcaccaac ccactaatca gacatgagaa cagaatggtg 540
ctggccagca ctacagctaa ggctatggag cagatggcgg gatcaagtga gcaggcagcg 600
gaagccatgg agatcgctaa tcaggctagg cagatggtgc aggcaatgag gacaattggg 660
actcatccta actctagtgc tggtctgaga gataatcttc ttgaaaattt gcaggcctac 720
cagaaacgaa tgggagtgca gatgcagcga ttcaagtga 759

<210> SEQ ID NO 41
<211> LENGTH: 793
<212> TYPE: DNA
<213> ORGANISM: Influenza virus

<400> SEQUENCE: 41
atatctgcag aattcgccct tagaattcga cgtcatgagt cttctaaccg aggtcgaaac 60
gtacgttctc tctatcatcc cgtcaggccc cctcaaagcc gagatcgcac agaaacttga 120
agatgtcttt gcaggaaaga acaccgatct cgaggctctc atggagtggc taaagacaag 180
accaatcctg tcacctctga ctaaagggat tttgggattt gtattcacgc tcaccgtgcc 240
cagtgagcga ggactgcagc gtagacgctt tgtccagaat gccctaaatg gaaatggaga 300
tccaaataat atggataggg cagttaagct atataagaag ctgaaaagag aaataacatt 360
ccatggggct aaggaggtcg cactcagcta ctcaaccggt gcacttgcca gttgcatggg 420
tctcatatac aacaggatgg gaacggtgac tacggaagtg gcttttggcc tagtgtgtgc 480
cacttgtgag cagattgcag attcacagca tcggtctcac agacagatgg caactatcac 540
caacccacta atcagacatg agaacagaat ggtgctggcc agcactacag ctaaggctat 600
ggagcagatg gcgggatcaa gtgagcaggc agcggaagcc atggagatcg ctaatcaggc 660
taggcagatg gtgcaggcaa tgaggacaat tgggactcat cctaactcta gtgctggtct 720
gagagataat cttcttgaaa atttgcaggc ctaccagaaa cgaatgggag tgcagatgca 780
gcgattcaag tga 793

<210> SEQ ID NO 42
<211> LENGTH: 1740
<212> TYPE: DNA
<213> ORGANISM: Artificial sequence
<220> FEATURE:
<223> OTHER INFORMATION: Influenza HA gene optimized for expression in
insect cell expression system

<400> SEQUENCE: 42
ggtaccggat ccgccaccat ggagaagatc gtgctgctgc tggctatcgt gtccctggtg 60
aagtccgacc agatctgcat cggttaccac gctaacaact ccaccgagca ggtggacacc 120
atcatggaga agaacgtcac cgtgacccac gctcaggaca tcctcgaaaa gacccacaac 180
ggcaagctgt gcgacctgga cggtgtcaag cccctgatcc tgcgtgactg ctccgtggct 240
ggttggctgc tgggtaaccc catgtgcgac gagttcatca acgtgcccga gtggtcctac 300
atcgtggaga aggctaaccc caccaacgac ctgtgctacc ccggttcctt caacgactac 360
gaggagctga agcacctgct gtcccgtatc aaccacttcg agaagatcca gatcatcccc 420
aagtcctctt ggtccgacca cgaggcttcc tccggtgtct cctccgcttg cccctacctg 480 ggttcccccct ccttcttccg taacgtggtg tggctgatca agaagaactc cacctacccc 540
accatcaaga agtcctacaa caacaccaac caggaggacc tgctggtcct gtggggtatc 600
caccacccca acgacgctgc cgagcagacc cgtctgtacc agaaccccac cacctacatc 660
tccatcggca cctccaccct gaaccagcgt ctggtgccca agatcgctac ccgttccaag 720
gtgaacggcc agtccggtcg tatggagttc ttctggacca tcctgaagcc taacgacgct 780
atcaacttcg agtccaacgg caacttcatc gctcccgagt acgcttacaa gatcgtgaag 840
aagggcgact ccgctatcat gaagtccgag ctggagtacg gtaactgcaa caccaagtgc 900
cagaccccca tgggtgctat caactcctcc atgcccttcc acaacatcca ccccctgacc 960
atcggcgagt gccccaagta cgtgaagtcc aaccgtctgg tgctggctac cggtctgcgt 1020
aactcccccc agcgcgagtc ccgtcgtaag aagcgtggtc tgttcggcgc tatcgctggt 1080
ttcatcgagg gcggttggca gggcatggtg gacggatggt acggttacca ccactctaac 1140
gagcagggtt ccggttacgc tgctgacaag gagtccaccc agaaggctat cgacggcgtc 1200
accaacaagg tgaactccat catcgacaag atgaacaccc agttcgaggc tgtgggtcgt 1260
gagttcaaca acctcgagcg tcgtatcgag aacctgaaca agaagatgga ggacggtttc 1320
ctggacgtgt ggacctacaa cgccgagctg ctggtgctga tggagaacga gcgtaccctg 1380
gacttccacg actccaacgt gaagaacctg tacgacaagg tccgcctgca gctgcgtgac 1440
aacgctaagg agctgggtaa cggttgcttc gagttctacc acaagtgcga caacgagtgc 1500
atggagtcca tccgtaacgg cacctacaac tacccccagt actccgagga ggctcgtctg 1560
aagcgtgagg agatctccgg cgtgaagctc gagtccatcg gaacctacca gatcctgtcc 1620
atctactcca ccgtggcttc ctccctggct ctggctatca tgatggctgg tctgtccctg 1680
tggatgtgct ccaacggttc cctgcagtgc cgtatctgca tctaatgaaa gcttgagctc 1740

<210> SEQ ID NO 43
<211> LENGTH: 568
<212> TYPE: PRT
<213> ORGANISM: Influenza virus

<400> SEQUENCE: 43

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

-continued

```
Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565
```

<210> SEQ ID NO 44
<211> LENGTH: 1716
<212> TYPE: DNA
<213> ORGANISM: Artificial Sequence
<220> FEATURE:
<223> OTHER INFORMATION: Influenza HA gene optimized for expression in insect cell expression system

<400> SEQUENCE: 44
ggatccgcca ccatggagaa gatcgtgctg ctgctggcta tcgtgtccct ggtgaagtcc 60
gaccagatct gcatcggtta ccacgctaac aactccaccg agcaggtgga caccatcatg 120
gagaagaacg tcaccgtgac ccacgctcag gacatcctcg aaaagaccca caacggcaag 180
ctgtgcgacc tggacggtgt caagcccctg atcctgcgtg actgctccgt ggctggttgg 240
ctgctgggta accccatgtg cgacgagttc atcaacgtgc ccgagtggtc ctacatcgtg 300
gagaaggcta accccaccaa cgacctgtgc taccccggtt ccttcaacga ctacgaggag 360
ctgaagcacc tgctgtcccg tatcaaccac ttcgagaaga tccagatcat ccccaagtcc 420
tcttggtccg accacgaggc ttcctccggt gtctcctccg cttgccccta cctgggttcc 480
ccctccttct tccgtaacgt ggtgtggctg atcaagaaga actccaccta ccccaccatc 540
aagaagtcct acaacaacac caaccaggag gacctgctgg tcctgtgggg tatccaccac 600
cccaacgacg ctgccgagca gacccgtctg taccagaacc ccaccaccta catctccatc 660
ggcacctcca ccctgaacca gcgtctggtg cccaagatcg ctacccgttc caaggtgaac 720
ggccagtccg gtcgtatgga gttcttctgg accatcctga agcctaacga cgctatcaac 780
ttcgagtcca acggcaactt catcgctccc gagtacgctt acaagatcgt gaagaagggc 840
gactccgcta tcatgaagtc cgagctggag tacggtaact gcaacaccaa gtgccagacc 900
cccatgggtg ctatcaactc ctccatgccc ttccacaaca tccacccccct gaccatcggc 960 gagtgcccca agtacgtgaa gtccaaccgt ctggtgctgg ctaccggtct gcgtaactcc 1020
ccccagcgcg agtcccgtgg tctgttcggc gctatcgctg gtttcatcga gggcggttgg 1080
cagggcatgg tggacggatg gtacggttac caccactcta acgagcaggg ttccggttac 1140
gctgctgaca aggagtccac ccagaaggct atcgacggcg tcaccaacaa ggtgaactcc 1200
atcatcgaca agatgaacac ccagttcgag gctgtgggtc gtgagttcaa caacctcgag 1260
cgtcgtatcg agaacctgaa caagaagatg gaggacggtt tcctggacgt gtggacctac 1320
aacgccgagc tgctggtgct gatggagaac gagcgtaccc tggacttcca cgactccaac 1380
gtgaagaacc tgtacgacaa ggtccgcctg cagctgcgtg acaacgctaa ggagctgggt 1440
aacggttgct tcgagttcta ccacaagtgc gacaacgagt gcatggagtc catccgtaac 1500
ggcacctaca actaccccca gtactccgag gaggctcgtc tgaagcgtga ggagatctcc 1560
ggcgtgaagc tcgagtccat cggaacctac cagatcctgt ccatctactc caccgtggct 1620
tcctccctgg ctctggctat catgatggct ggtctgtccc tgtggatgtg ctccaacggt 1680
tccctgcagt gccgtatctg catctaatga aagctt 1716

<210> SEQ ID NO 45
<211> LENGTH: 564
<212> TYPE: PRT
<213> ORGANISM: Influenza virus

<400> SEQUENCE: 45

Met Glu Lys Ile Val Leu Leu Leu Ala Ile Val Ser Leu Val Lys Ser
1 5 10 15

```
Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430
```

-continued

```
Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Ile Arg Asn
                485                 490                 495

Gly Thr Tyr Asn Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
    530                 535                 540

Met Ala Gly Leu Ser Leu Trp Met Cys Ser Asn Gly Ser Leu Gln Cys
545                 550                 555                 560

Arg Ile Cys Ile


<210> SEQ ID NO 46
<211> LENGTH: 1383
<212> TYPE: DNA
<213> ORGANISM: Artificial Sequence
<220> FEATURE:
<223> OTHER INFORMATION: Influenza NA gene optimized for expression in
      insect cell expression system

<400> SEQUENCE: 46

ggtaccggat ccgccaccat gaaccccaac cagaagatca tcaccatcgg ctccatctgc     60

atggtgatcg gtatcgtgtc cctgatgctg cagatcggta acatgatctc catctgggtg    120

tcccactcca tccagaccgg taaccagcac caggctgagt ccatctccaa caccaacccc    180

ctgaccgaga aggctgtggc ttccgtgacc ctggctggta actcctccct gtgccccatc    240

cgtggttggg ctgtgcactc caaggacaac aacatccgca tcggttccaa gggtgacgtg    300

ttcgtgatcc gtgagccctt catctcctgc tcccacctcg agtgccgtac cttcttcctg    360

acccaaggtg ctctgctgaa cgacaagcac tccaacggca ccgtgaagga ccgttccccc    420

caccgtaccc tgatgtcctg ccccgtgggc gaggctccct cccccctacaa ctcccgtttc    480

gagtccgtgg cttggtccgc ttccgcttgc cacgacggca cctcttggct gaccatcggt    540

atctccggtc ccgacaacga ggctgtcgct gtgctgaagt acaacggcat catcaccgac    600

accatcaagt cctggcgtaa caacatcctg cgtacccagg agtccgagtg cgcttgcgtg    660

aacggttcct gcttcaccgt gatgaccgac ggtccctccg acggccaggc ttcctacaag    720

atcttcaaga tggagaaggg caaggtggtg aagtccgtgg agctggacgc tcccaactac    780

cactacgagg agtgctcttg ctaccccgac gctggcgaga tcacctgcgt gtgccgtgac    840

aactggcacg gttccaaccg tccctgggtg tccttcaacc agaacctcga gtaccagatc    900

ggttacatct gctccggcgt gttcggtgac aacccccgtc ccaacgacgg aaccggttcc    960

tgcggtccca tgtcccccaa cggtgcttac ggtgtcaagg gcttctcctt caagtacggt   1020

aacggtgtct ggatcggtcg taccaagtcc accaactccc gctccggttt cgagatgatc   1080

tgggacccca acggttggac cggcaccgac tcttccttct ccgtgaagca ggacatcgtg   1140

gctatcaccg actggtccgg ttactccggt tccttcgtgc agcaccccga gctgaccggt   1200

ctggactgca ttcgtccctg cttctgggtg gagctgatcc gtggtcgtcc caaggagtcc   1260
```

```
accatctgga cctccggctc ctccatctct ttctgcggtg tgaactccga caccgtgtcc   1320

tggtcctggc ccgacggtgc cgagctgccc ttcaccatcg acaagtaatg aaagcttgag   1380

ctc                                                                 1383


<210> SEQ ID NO 47
<211> LENGTH: 449
<212> TYPE: PRT
<213> ORGANISM: Influenza virus

<400> SEQUENCE: 47

Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ile
            20                  25                  30

Trp Val Ser His Ser Ile Gln Thr Gly Asn Gln His Gln Ala Glu Ser
        35                  40                  45

Ile Ser Asn Thr Asn Pro Leu Thr Glu Lys Ala Val Ala Ser Val Thr
    50                  55                  60

Leu Ala Gly Asn Ser Ser Leu Cys Pro Ile Arg Gly Trp Ala Val His
65                  70                  75                  80

Ser Lys Asp Asn Asn Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Glu Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asp Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Met Ser Pro
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350
```

```
Met Ile Trp Asp Pro Asn Gly Trp Thr Gly Thr Asp Ser Ser Phe Ser
        355                 360                 365

Val Lys Gln Asp Ile Val Ala Ile Thr Asp Trp Ser Gly Tyr Ser Gly
    370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430

Val Ser Trp Ser Trp Pro Asp Gly Ala Glu Leu Pro Phe Thr Ile Asp
        435                 440                 445

Lys


<210> SEQ ID NO 48
<211> LENGTH: 792
<212> TYPE: DNA
<213> ORGANISM: Artificial Sequence
<220> FEATURE:
<223> OTHER INFORMATION: Influenza M1 gene optimized for expression in
      insect cell expression system

<400> SEQUENCE: 48

ggtaccggat ccgccaccat gtccctgctg accgaggtgg agacctacgt gctgtccatc     60

atcccctccg gtcctctgaa ggctgagatc gctcagaagc tcgaggacgt tttcgctggc    120

aagaacaccg acctcgaggc tctgatggag tggctcaaga cccgtcccat cctgtccccc    180

ctgaccaagg gtatcctggg tttcgtgttc accctgaccg tgccctccga gcgtggtctg    240

cagcgtcgtc gtttcgtgca gaacgctctg aacggtaacg gtgaccccaa caacatggac    300

cgtgctgtga agctgtacaa gaagctgaag cgcgagatca ccttccacgg tgctaaggag    360

gtgtccctgt cctactccac cggtgctctg gctagctgca tgggcctgat ctacaaccgt    420

atgggcaccg tgaccaccga ggtggccttc ggtctggtct gcgctacctg cgagcagatc    480

gctgactccc agcaccgttc ccaccgtcag atggctacca tcaccaaccc cctgatccgt    540

cacgagaacc gtatggtgct ggcttccacc accgctaagg ctatggagca gatggctggt    600

tcctccgagc aggctgctga ggccatggag gtggccaacc aggctcgtca gatggtgcag    660

gctatgcgta ccatcggcac ccacccccaac tcctccgctg gtctgcgtga caacctgctc    720

gagaacctgc aggcttacca gaagcgtatg ggagtccaga tgcagcgctt caagtaatga    780

aagcttgagc tc                                                        792


<210> SEQ ID NO 49
<211> LENGTH: 252
<212> TYPE: PRT
<213> ORGANISM: Influenza virus

<400> SEQUENCE: 49

Met Ser Leu Leu Thr Glu Val Glu Thr Tyr Val Leu Ser Ile Ile Pro
1               5                   10                  15

Ser Gly Pro Leu Lys Ala Glu Ile Ala Gln Lys Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60
```

```
Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ser Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Ala Thr Ile Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Asn Gln
        195                 200                 205

Ala Arg Gln Met Val Gln Ala Met Arg Thr Ile Gly Thr His Pro Asn
    210                 215                 220

Ser Ser Ala Gly Leu Arg Asp Asn Leu Leu Glu Asn Leu Gln Ala Tyr
225                 230                 235                 240

Gln Lys Arg Met Gly Val Gln Met Gln Arg Phe Lys
                245                 250
```

<210> SEQ ID NO 50
<211> LENGTH: 1736
<212> TYPE: DNA
<213> ORGANISM: Artificial Sequence
<220> FEATURE:
<223> OTHER INFORMATION: Influenza HA gene optimized for expression in insect cell expression system

<400> SEQUENCE: 50

```
ggtaccggat ccctcgagat ggagaagatc gtgctgctgc tggctatcgt gtccctggtg     60

aagtccgacc agatctgcat cggttaccac gctaacaact ccaccgagca ggtggacacc    120

atcatggaga agaacgtcac cgtgacccac gctcaggaca tcctggaaaa gacccacaac    180

ggcaagctgt gcgacctgga cggtgtcaag cccctgatcc tgcgtgactg ctccgtggct    240

ggttggctgc tgggtaaccc catgtgcgac gagttcatca acgtgcccga gtggtcctac    300

atcgtggaga aggctaaccc cgctaacgac ctgtgctacc ccggtaactt caacgactac    360

gaggagctga agcacctgct gtcccgtatc aaccacttcg agaagatcca gatcatcccc    420

aagtcctctt ggtccgacca cgaggcttcc tccggtgtct cctccgcttg cccataccag    480

ggcaccccat ctttcttccg taacgtggtg tggctgatca agaagaacaa cacctacccc    540

accatcaagc gttcctacaa caacaccaac caggaggacc tgctgatcct gtggggtatc    600

caccactcca acgacgctgc cgagcagacc aagctgtacc agaaccccac cacctacatc    660

tccgtgggca cctccaccct gaaccagcgt ctggtgccca agatcgctac ccgttccaag    720

gtgaacggcc agtccggtcg tatggacttc ttctggacca tcctgaagcc taacgacgct    780

atcaacttcg agtccaacgg caacttcatc gctcccgagt acgcttacaa gatcgtgaag    840

aagggcgact ccgctatcgt caagtccgag gtggagtacg gtaactgcaa caccaagtgc    900

cagaccccca tcggtgctat caactcctcc atgcccttcc acaacatcca cccccctgacc    960
```

```
atcggcgagt gccccaagta cgtgaagtcc aacaagctgg tgctggctac cggtctgcgt   1020

aactcccccc tgcgtgagcg tggtctgttc ggcgctatcg ctggtttcat cgagggcggt   1080

tggcagggca tggtggacgg ttggtacggt taccaccaca gcaacgagca gggttccggt   1140

tacgctgctg acaaggagtc cacccagaag gctatcgacg gcgtcaccaa caaggtgaac   1200

tccatcatcg acaagatgaa cacccagttc gaggctgtgg gtcgtgagtt caacaacctg   1260

gagcgtcgta tcgagaacct gaacaagaag atggaggacg gtttcctgga cgtgtggacc   1320

tacaacgccg agctgctggt gctgatggag aacgagcgta ccctggactt ccacgactct   1380

aacgtgaaga acctgtacga caaggtccgc ctgcagctgc gtgacaacgc taaggagctg   1440

ggtaacggtt gcttcgagtt ctaccacaag tgcgacaacg agtgcatgga gtccgtgcgt   1500

aacggcacct acgactaccc ccagtactcc gaggaggctc gtctgaagcg tgaggagatc   1560

tccggcgtga agctggagtc catcggcacc taccagatcc tgtccatcta ctccaccgtg   1620

gcttcctccc tggctctggc tatcatggtg gctggtctgt ccctgtggat gtgctccaac   1680

ggttccctgc agtgccgtat ctgcatctaa taatgaggcg cgccaagctt gagctc         1736
```

```
<210> SEQ ID NO 51
<211> LENGTH: 563
<212> TYPE: PRT
<213> ORGANISM: Influenza virus

<400> SEQUENCE: 51

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240
```

```
Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Val Lys Ser Glu Val Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Gly Leu Phe Gly Ala Ile Ala Gly Phe Ile Glu
            340                 345                 350

Gly Gly Trp Gln Gly Met Val Asp Gly Trp Tyr Gly Tyr His His Ser
        355                 360                 365

Asn Glu Gln Gly Ser Gly Tyr Ala Ala Asp Lys Glu Ser Thr Gln Lys
    370                 375                 380

Ala Ile Asp Gly Val Thr Asn Lys Val Asn Ser Ile Ile Asp Lys Met
385                 390                 395                 400

Asn Thr Gln Phe Glu Ala Val Gly Arg Glu Phe Asn Asn Leu Glu Arg
                405                 410                 415

Arg Ile Glu Asn Leu Asn Lys Lys Met Glu Asp Gly Phe Leu Asp Val
            420                 425                 430

Trp Thr Tyr Asn Ala Glu Leu Leu Val Leu Met Glu Asn Glu Arg Thr
        435                 440                 445

Leu Asp Phe His Asp Ser Asn Val Lys Asn Leu Tyr Asp Lys Val Arg
    450                 455                 460

Leu Gln Leu Arg Asp Asn Ala Lys Glu Leu Gly Asn Gly Cys Phe Glu
465                 470                 475                 480

Phe Tyr His Lys Cys Asp Asn Glu Cys Met Glu Ser Val Arg Asn Gly
                485                 490                 495

Thr Tyr Asp Tyr Pro Gln Tyr Ser Glu Glu Ala Arg Leu Lys Arg Glu
            500                 505                 510

Glu Ile Ser Gly Val Lys Leu Glu Ser Ile Gly Thr Tyr Gln Ile Leu
        515                 520                 525

Ser Ile Tyr Ser Thr Val Ala Ser Ser Leu Ala Leu Ala Ile Met Val
    530                 535                 540

Ala Gly Leu Ser Leu Trp Met Cys Ser Asn Gly Ser Leu Gln Cys Arg
545                 550                 555                 560

Ile Cys Ile
```

```
<210> SEQ ID NO 52
<211> LENGTH: 1738
<212> TYPE: DNA
<213> ORGANISM: Artificial Sequence
<220> FEATURE:
<223> OTHER INFORMATION: Influenza HA gene optimized for expression in
      insect cell expression system

<400> SEQUENCE: 52

cgggcgcgga gcggccgcat ggagaagatc gtgctgctgc tggctatcgt gtctctggtc      60

aagtccgacc agatctgcat cggttaccac gctaacaact ccaccgagca ggtggacacc     120

atcatggaga agaacgtcac cgtgacccac gctcaggaca tcctcgaaaa gacccacaac     180
```

```
ggcaagctgt gcgacctgga cggcgtgaag cccctgatcc tgcgtgactg ctccgtggct    240
ggttggctgc tgggtaaccc catgtgcgac gagttcctca acgtgcccga gtggtcctac    300
atcgtggaga agatcaaccc cgctaacgac ctgtgctacc ccggtaactt caacgactac    360
gaggagctga agcacctgct gtcccgtatc aaccacttcg agaagatcca gatcatcccc    420
aagtcctctt ggtccgacca cgaggcttcc tccggtgtct cctccgcttg cccataccag    480
ggccgttctt ccttcttccg caacgtggtg tggctgatca agaagaacaa cgcctacccc    540
accatcaagc gttcctacaa caacaccaac caggaggacc tgctggtcct gtggggtatc    600
caccacccca acgacgctgc cgagcagacc cgtctgtacc agaaccccac cacctacatc    660
tccgtgggca cctctaccct gaaccagcgt ctggtgccca agatcgctac ccgttccaag    720
gtgaacggcc agtccggtcg tatggagttc ttctggacca tcctgaagcc taacgacgct    780
atcaacttcg agtccaacgg caacttcatc gctcccgaga acgcttacaa gatcgtgaag    840
aagggcgact ccaccatcat gaagtccgag ctggagtacg gcaactgcaa cactaagtgc    900
cagaccccca tcggtgctat caactcctcc atgcccttcc acaacatcca ccccctgact    960
atcggcgagt gccccaagta cgtgaagtcc aaccgtctgg tgctggctac cggtctgcgt   1020
aactcccccc agatcgagac tcgtggtctg ttcggcgcta tcgctggttt catcgagggc   1080
ggttggcagg gcatggtgga cggttggtac ggttaccacc actctaacga gcagggttcc   1140
ggttacgctg ctgacaagga gtctacccag aaggctatcg acggcgtcac caacaaggtg   1200
aactccatca tcgacaagat gaacacccag ttcgaggctg tgggtcgtga gttcaacaac   1260
ctcgaacgtc gtatcgagaa cctgaacaag aagatggagg acggtttcct ggacgtgtgg   1320
acctacaacg ccgagctgct ggtgctgatg gagaacgagc gtaccctgga cttccacgac   1380
tccaacgtga agaacctgta cgacaaggtc cgcctgcagc tgcgtgacaa cgctaaggag   1440
ctgggtaacg gttgcttcga gttctaccac cgttgcgaca acgagtgcat ggagtccgtg   1500
cgtaacggca cctacgacta cccccagtac tccgaggagg ctcgtctgaa gcgtgaggag   1560
atctccggtg tcaagctcga atccatcgga acctaccaga tcctgtccat ctactccacc   1620
gtggcttcct ccctggctct ggctatcatg gtggctggtc tgtccctgtg gatgtgctcc   1680
aacggttccc tgcagtgccg tatctgcatc taataatgag gcgcgccaag cttgtcga     1738
```

<210> SEQ ID NO 53
<211> LENGTH: 564
<212> TYPE: PRT
<213> ORGANISM: Influenza virus

<400> SEQUENCE: 53

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95
```

-continued

```
Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Ile Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Arg Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
```

515 520 525

Leu Ser Ile Tyr Ser Thr Val Ala Ser Ser Leu Ala Leu Ala Ile Met
530 535 540

Val Ala Gly Leu Ser Leu Trp Met Cys Ser Asn Gly Ser Leu Gln Cys
545 550 555 560

Arg Ile Cys Ile

<210> SEQ ID NO 54
<211> LENGTH: 1422
<212> TYPE: DNA
<213> ORGANISM: Artificial Sequence
<220> FEATURE:
<223> OTHER INFORMATION: Influenza NA gene optimized for expression in insect cell expression system

<400> SEQUENCE: 54
accgtcccac catcgggcgc ggatccctcg agatgaaccc caaccagaag atcatcacca 60
tcggctccat ctgcatggtg atcggtatcg tgtccctgat gctgcagatc ggtaacatga 120
tctccatctg ggtgtcccac tccatccaga ccggtaacca gcgtcaggcc gagcccatct 180
ccaacaccaa gttcctcacc gagaaggctg tggcttccgt gaccctggct ggtaactcct 240
ccctgtgccc catctccggt tgggctgtgt actccaagga caactccatc cgtatcggtt 300
cccgtggtga cgtgttcgtg atccgtgagc ccttcatctc ctgctcccac ctcgaatgcc 360
gtaccttctt cctgacccag ggtgctctgc tgaacgacaa gcactccaac ggcaccgtga 420
aggaccgttc cccccaccgt accctgatgt cctgccccgt gggcgaggct ccctccccct 480
acaactcccg tttcgagtcc gtggcttggt ccgcttccgc ttgccacgac ggcacctctt 540
ggctgaccat cggtatctcc ggtcccgaca acggtgctgt ggctgtgctg aagtacaacg 600
gcatcatcac cgacaccatc aagtcctggc gtaacaacat cctgcgtacc caagagtccg 660
agtgcgcttg cgtgaacggt tcctgcttca ccgtgatgac cgacggtccc tccaacggcc 720
aggcttccta caagatcttc aagatggaga agggcaaggt ggtgaagtcc gtggagctgg 780
acgctcccaa ctaccactac gaggagtgct cttgctaccc cgacgctggc gagatcacct 840
gcgtgtgccg tgacaactgg cacggttcca accgtccctg ggtgtccttc aaccagaacc 900
tcgaatacca gatcggttac atctgctccg gcgtgttcgg tgacaacccc cgtcccaacg 960
acggaaccgg ttcctgcggt cccgtgtccc ccaacggtgc ttacggtgtc aagggcttct 1020
ccttcaagta cggtaacggt gtctggatcg gtcgtaccaa gtccaccaac tcccgctccg 1080
gtttcgagat gatctgggac cccaacggtt ggaccggcac cgactcttcc ttctccgtga 1140
agcaggacat cgtggctatc accgactggt ccggttactc cggttccttc gtgcagcacc 1200
ccgagctgac cggtctggac tgtatccgtc cctgcttctg ggtggagctg atccgtggtc 1260
gtcccaagga gtccaccatc tggacctccg gctcctccat ctctttctgc ggtgtgaact 1320
ccgacaccgt gtcctggtcc tggcccgacg gtgccgagct gcccttcacc atcgacaagt 1380
aataatgaat cgatttgtcg agaagtacta gaggatcata at 1422

<210> SEQ ID NO 55
<211> LENGTH: 449
<212> TYPE: PRT
<213> ORGANISM: Influenza virus

<400> SEQUENCE: 55

Met Asn Pro Asn Gln Lys Ile Ile Thr Ile Gly Ser Ile Cys Met Val
1 5 10 15

-continued

```
Ile Gly Ile Val Ser Leu Met Leu Gln Ile Gly Asn Met Ile Ser Ile
            20                  25                  30

Trp Val Ser His Ser Ile Gln Thr Gly Asn Gln Arg Gln Ala Glu Pro
        35                  40                  45

Ile Ser Asn Thr Lys Phe Leu Thr Glu Lys Ala Val Ala Ser Val Thr
    50                  55                  60

Leu Ala Gly Asn Ser Ser Leu Cys Pro Ile Ser Gly Trp Ala Val Tyr
65                  70                  75                  80

Ser Lys Asp Asn Ser Ile Arg Ile Gly Ser Arg Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Pro
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Gly Thr Asp Ser Ser Phe Ser
        355                 360                 365

Val Lys Gln Asp Ile Val Ala Ile Thr Asp Trp Ser Gly Tyr Ser Gly
    370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430
```

-continued

Val Ser Trp Ser Trp Pro Asp Gly Ala Glu Leu Pro Phe Thr Ile Asp
435 440 445

Lys

<210> SEQ ID NO 56
<211> LENGTH: 1750
<212> TYPE: DNA
<213> ORGANISM: Influenza virus

<400> SEQUENCE: 56
attcgccctt aacggtccga tggagaaaat agtgcttctt cttgcaatag tcagtcttgt 60
taaaagtgat cagatttgca ttggttacca tgcaaacaat tcaacagagc aggttgacac 120
aatcatggaa aagaacgtta ctgttacaca tgcccaagac atactggaaa agacacacaa 180
cgggaagctc tgcgatctag atggagtgaa gcctctaatt ttaagagatt gtagtgtagc 240
tggatggctc ctcgggaacc caatgtgtga cgaattcatc aatgtaccgg aatggtctta 300
catagtggag aaggccaatc caaccaatga cctctgttac ccagggagtt tcaacgacta 360
tgaagaactg aaacacctat tgagcagaat aaaccatttt gagaaaattc aaatcatccc 420
caaaagttct tggtccgatc atgaagcctc atcaggagtg agctcagcat gtccatacct 480
gggaagtccc tcctttttta gaaatgtggt atggcttatc aaaaagaaca gtacataccc 540
aacaataaag aaaagctaca ataataccaa ccaagaagat cttttggtac tgtggggaat 600
tcaccatcct aatgatgcgg cagagcagac aaggctatat caaaacccaa ccacctatat 660
ttccattggg acatcaacac taaaccagag attggtacca aaaatagcta ctagatccaa 720
agtaaacggg caaagtggaa ggatggagtt cttctggaca attttaaaac ctaatgatgc 780
aatcaacttc gagagtaatg gaaatttcat tgctccagaa tatgcataca aaattgtcaa 840
gaaaggggac tcagcaatta tgaaaagtga attggaatat ggtaactgca acaccaagtg 900
tcaaactcca atgggggcga taaactctag tatgccattc cacaacatac accctctcac 960
catcggggaa tgccccaaat atgtgaaatc aaacagatta gtccttgcaa cagggctcag 1020
aaatagccct caaagagaga gcagaagaaa aaagagagga ctatttggag ctatagcagg 1080
ttttatagag ggaggatggc agggaatggt agatggttgg tatgggtacc accatagcaa 1140
tgagcagggg agtgggtacg ctgcagacaa agaatccact caaaaggcaa tggatggagt 1200
caccaataag gtcaactcaa tcattgacaa aatgaacact cagtttgagg ccgttggaag 1260
ggaatttaat aacttagaaa ggagaataga gaatttaaac aagaagatgg aagacgggtt 1320
tctagatgtc tggacttata atgccgaact tctggttctc atggaaaatg agagaactct 1380
agactttcat gactcaaatg ttaagaacct ctacgacaag gtccgactac agcttaggga 1440
taatgcaaag gagctgggta acggttgttt cgagttctat cacaaatgtg ataatgaatg 1500
tatggaaagt ataagaaacg gaacgtgcaa ctatccgcag tattcagaag aagcaagatt 1560
aaaaagagag gaaataagtg gggtaaaatt ggaatcaata ggaacttacc aaatactgtc 1620
aatttattca acagtggcga gttccctagc actggcaatc atgatggctg gtctatcttt 1680
atggatgtgc tccaatggat cgttacaatg cagaatttgc atttaaaagc tttaagggcg 1740
aattccagca 1750

<210> SEQ ID NO 57
<211> LENGTH: 568
<212> TYPE: PRT
<213> ORGANISM: Influenza virus

<400> SEQUENCE: 57

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Met Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415
```

```
Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Cys Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565


<210> SEQ ID NO 58
<211> LENGTH: 568
<212> TYPE: PRT
<213> ORGANISM: Influenza virus

<400> SEQUENCE: 58

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
```

-continued

```
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565
```

FUNCTIONAL INFLUENZA VIRUS-LIKE PARTICLES (VLPS)

CROSS-REFERENCE TO RELATED APPLICATIONS

This application is a continuation of U.S. Ser. No. 13/796,125, filed Mar. 12, 2013, which is a continuation of U.S. Ser. No. 10/617,569 filed Jul. 11, 2003, now U.S. Pat. No. 8,592,197, each of which is incorporated herein in its entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: "NOVV_003_02_US_SeqList.txt" date recorded: Mar. 11, 2013, file size 9 kb).

BACKGROUND OF INVENTION

Influenza virus is a member of Orthomyxoviridae family (for review, see Murphy and Webster, 1996). There are three subtypes of influenza viruses designated A, B, and C. The influenza virion contains a segmented negative-sense RNA genome. The influenza virion includes the following proteins: hemagglutinin (HA), neuraminidase (NA), matrix (M1), proton ion-channel protein (M2), nucleoprotein (NP), polymerase basic protein 1 (PB1), polymerase basic protein 2 (PB2), polymerase acidic protein (P A), and nonstructural protein 2 (NS2) proteins. The HA, NA, M1, and M2 are membrane associated, whereas NP, PB 1, PB2, P A, and NS2 are nucleocapsid associated proteins. The NS 1 is the only nonstructural protein not associated with virion particles but specific for influenza-infected cells. The M1 protein is the most abundant protein in influenza particles. The HA and NA proteins are envelope glycoproteins, responsible for virus attachment and penetration of the viral particles into the cell, and the sources of the major immunodominant epitopes for virus neutralization and protective immunity. Both HA and NA proteins are considered the most important components for prophylactic influenza vaccines.

Influenza virus infection is initiated by the attachment of the virion surface HA protein to a sialic acid-containing cellular receptor (glycoproteins and glycolipids). The NA protein mediates processing of the sialic acid receptor, and virus penetration into the cell depends on HA-dependent receptor-mediated endocytosis. In the acidic confines of internalized endosomes containing an influenza virion, the $HA_2$ protein undergoes conformational changes that lead to fusion of viral and cell membranes and virus uncoating and M2-mediated release of M1 proteins from nucleocapsid-associated ribonucleoproteins (RNPs), which migrate into the cell nucleus for viral RNA synthesis. Antibodies to HA proteins prevent virus infection by neutralizing virus infectivity, whereas antibodies to NA proteins mediate their effect on the early steps of viral replication.

Inactivated influenza A and B virus vaccines are licensed currently for parenteral administration. These trivalent vaccines are produced in the allantoic cavity of embryonated chick eggs, purified by rate zonal centrifugation or column chromatography, inactivated with formalin or β-propiolactone, and formulated as a blend of the two strains of type A and the type B strain of influenza viruses in circulation among the human population for a given year. The available commercial influenza vaccines are whole virus (WV) or subvirion (SV; split or purified surface antigen) virus vaccines. The WV vaccine contains intact, inactivated virions. SV vaccines treated with solvents such as tri-n-butyl phosphate (Flu-Shield, Wyeth-Lederle) contain nearly all of the viral structural proteins and some of the viral envelopes. SV vaccines solubilized with Triton X-100 (Fluzone, Connaught; Fluvirin, Evans) contain aggregates of HA monomers, NA, and NP principally, although residual amounts of other viral structural proteins are present. A potential cold-adapted live attenuated influenza virus vaccine (FluMist, MedImmune) was granted marketing approval recently by the FDA for commercial usage as an intranasally delivered vaccine indicated for active immunization and the prevention of disease caused by influenza A and B viruses in healthy children and adolescents, 5-17 years of age and healthy adults 18-49 years of age.

Several recombinant products have been developed as recombinant influenza vaccine candidates. These approaches have focused on the expression, production, and purification of influenza type A HA and NA proteins, including expression of these proteins using baculovirus infected insect cells (Crawford et al, 1999; Johansson, 1999; Treanor et al., 1996), viral vectors (Pushko et al., 1997; Berglund et al, 1999), and DNA vaccine constructs (Olsen et al., 1997).

Crawford et al. (1999) demonstrated that influenza HA expressed in baculovirus infected insect cells is capable of preventing lethal influenza disease caused by avian H5 and H7 influenza subtypes. At the same time, another group demonstrated that baculovirus-expressed influenza HA and NA proteins induce immune responses in animals superior to those induced by a conventional vaccine (Johansson et al., 1999). Immunogenicity and efficacy of baculovirus-expressed hemagglutinin of equine influenza virus was compared to a homologous DNA vaccine candidate (Olsen et al., 1997). Taken together, the data demonstrated that a high degree of protection against influenza virus challenge can be induced with recombinant HA or NA proteins, using various experimental approaches and in different animal models.

Lakey et al. (1996) showed that a baculovirus-derived influenza HA vaccine was well-tolerated and immunogenic in human volunteers in a Phase I dose escalation safety study. However, results from Phase II studies conducted at several clinical sites in human volunteers vaccinated with several doses of influenza vaccines comprised of HA and/or NA proteins indicated that the recombinant subunit protein vaccines did not elicit protective immunity [G. Smith, Protein Sciences; M. Perdue, USDA, Personal Communications]. These results indicated that conformational epitopes displayed on the surface of HA and NA peplomers of infectious virions were important in the elicitation of neutralizing antibodies and protective immunity.

Regarding the inclusion of other influenza proteins in recombinant influenza vaccine candidates, a number of studies have been carried out, including the experiments involving influenza nucleoprotein, NP, alone or in combination with M1 protein (Ulmer et al., 1993; Ulmer et al., 1998; Zhou et al., 1995; Tsui et al., 1998). These vaccine candidates, which were composed of quasi-invariant inner virion proteins, elicited a broad spectrum immunity that was primarily cellular (both $CD4^+$ and $CD8^+$ memory T cells). These experiments involved the use of the DNA or viral genetic vectors. Relatively large amounts of injected DNA were needed, as results from experiments with lower doses of DNA indicated little or no protection (Chen et al., 1998).

Hence, further preclinical and clinical research may be required to evaluate whether such DNA-based approaches involving influenza NP and M1 are safe, effective, and persistent.

Recently, in an attempt to develop more effective vaccines for influenza, particulate proteins were used as carriers of influenza M2 protein epitopes. The rationale for development of an M2-based vaccine was that in animal studies protective immunity against influenza was elicited by M2 proteins (Slepushkin et al., 1995). Neirynck et al. (1999) used a 23-aa long M2 transmembrane domain as an amino terminal fusion partner with the hepatitis B virus core antigen (HBcAg) to expose the M2 epitope(s) on the surface of HBcAg capsid-like particles. However, in spite of the fact that both full-length M2 protein and M2-HBcAg VIP induced detectable antibodies and protection in mice, it was unlikely that future influenza vaccines would be based exclusively on the M2 protein, as the M2 protein was present at low copy number per virion, was weakly antigenic, was unable to elicit antibodies that bound free influenza virions, and was unable to block virus attachment to cell receptors (i.e. virus neutralization).

Since previous research has shown that the surface influenza glycoproteins, HA and NA, are the primary targets for elicitation of protective immunity against influenza virus and that M1 provides a conserved target for cellular immunity to influenza, a new vaccine candidate may include these viral antigens as a protein macromolecular particle, such as virus-like particles (VLPs). Further, the particle with these influenza antigens may display conformational epitopes that elicit neutralizing antibodies to multiple strains of influenza viruses.

Several studies have demonstrated that recombinant influenza proteins could self-assemble into VLPs in cell culture using mammalian expression plasmids or baculovirus vectors (Gomez-Puertas et al., 1999; Neumann et al., 2000; Latham and Galarza, 2001). Gomez-Puertas et al. (1999) demonstrated that efficient formation of influenza VLP depends on the expression levels of viral proteins. Neumann et al. (2000) established a mammalian expression plasmid-based system for generating infectious influenza virus-like particles entirely from cloned cDNAs. Latham and Galarza (2001) reported the formation of influenza VLPs in insect cells infected with recombinant baculovirus co-expressing HA, NA, M1, and M2 genes. These studies demonstrated that influenza virion proteins may self-assemble upon co-expression in eukaryotic cells.

SUMMARY OF INVENTION

According to the present invention, macromolecular protein structures are provided that comprise avian influenza virus type A H9N2 coding sequences for HA (GenBank Accession No. AJ404626), NA (GenBank Accession No. AJ404629), M1 (GenBank Accession No. AJ278646), M2 (GenBank Accession No. AF255363), and NP (GenBank Accession No. AF255742) proteins and that comprise human influenza virus type A H3N2 coding sequences for HA (GenBank Accession No. AJ311466) and for NA (GenBank Accession No. AJ291403). The genomic RNA encoding these influenza viral genes may be isolated from influenza virus isolates or from tissues of influenza-infected organisms. Each of these coding sequences from the same or different strains or types of influenza virus is cloned downstream of transcriptional promoters within expression vectors and are expressed in cells.

Thus, the invention provides a macromolecular protein structure containing (a) a first influenza virus M1 protein and (b) an additional structural protein, which may include a second or more influenza virus M1 protein; a first, second or more influenza virus HA protein; a first, second, or more influenza virus NA protein; and a first, second, or more influenza virus M2 protein. If the additional structural protein is not from a second or more influenza virus M1 protein, then both or all members of the group, e.g., first and second influenza M2 virus proteins are included. As such, there is provided a functional influenza protein structure, including a subviral particle, VLP, or capsomer structure, or a portion thereof, a vaccine, a multivalent vaccine, and mixtures thereof consisting essentially of influenza virus structural proteins produced by the method of the invention. In a particularly preferred embodiment, the influenza macromolecular protein structure includes influenza virus HA, NA, and M1 proteins that are the expression products of influenza virus genes cloned as synthetic fragments from a wild type virus.

The macromolecular protein structure may also include an additional structural protein, for example, a nucleoprotein (NP), membrane proteins from species other than noninfluenza viruses and a membrane protein from a non-influenza source, which are derived from avian or mammalian origins and different subtypes of influenza virus, including subtype A and B influenza viruses. The invention may include a chimeric macromolecular protein structure, which includes a portion of at least one protein having a moiety not produced by influenza virus.

Prevention of influenza may be accomplished by providing a macromolecular protein structure that may be self-assembled in a host cell from a recombinant construct. The macromolecular protein structure of the invention has the ability to self-assemble into homotypic or heterotypic virus-like particles (VLPs) that display conformational epitopes on HA and NA proteins, which elicit neutralizing antibodies that are protective. The composition may be a vaccine composition, which also contains a carrier or diluent and/or an adjuvant. The functional influenza VLPs elicit neutralizing antibodies against one or more strains or types of influenza virus depending on whether the functional influenza VLPs contain HA and/or NA proteins from one or more viral strains or types. The vaccine may include influenza virus proteins that are wild type influenza virus proteins. Preferably, the structural proteins containing the influenza VLP, or a portion of thereof, may be derived from the various strains of wild type influenza viruses. The influenza vaccines may be administered to humans or animals to elicit protective immunity against one or more strains or types of influenza virus.

The macromolecular protein structures of the invention may exhibit hemagglutinin activity and/or neuraminidase activity.

The invention provides a method for producing a VLP derived from influenza by constructing a recombinant construct that encodes influenza structural genes, including M1, HA, and at least one structural protein derived from influenza virus. A recombinant construct is used to transfect, infect, or transform a suitable host cell with the recombinant baculovirus. The host cell is cultured under conditions which permit the expression of M1, HA and at least one structural protein derived from influenza virus and the VLP is formed in the host cell. The infected cell media containing a functional influenza VLP is harvested and the VLP is purified. The invention also features an additional step of co-transfecting, co-infecting or co-transforming the host cell with a second recombinant construct which encodes a second influenza protein, thereby incorporating the second influenza protein within the VLP. Such structural proteins may be derived from influenza virus, including NA, M2, and NP, and at least one structural protein is derived from avian or mammalian origins. The structural protein may be a subtype A and B influenza viruses. According to the invention, the host cell may be a eukaryotic cell. In addition, the VLP may be a chimeric VLP.

The invention also features a method of formulating a drug substance containing an influenza VLP by introducing recombinant constructs encoding influenza viral genes into host cells and allowing self-assembly of the recombinant influenza viral proteins into a functional homotypic or heterotypic VLP in cells. The influenza VLP is isolated and purified and a drug substance is formulated containing the influenza VLP. The drug substance may further include an adjuvant. In addition, the invention provides a method for formulating a drug product, by mixing such a drug substance containing an influenza VLP with a lipid vesicle, i.e., a non-ionic lipid vesicle. Thus, functional homotypic or heterotypic VLPs may bud as enveloped particles from the infected cells. The budded influenza VLPs may be isolated and purified by ultracentrifugation or column chromatography as drug substances and formulated alone or with adjuvants such as Novasomes®, a product of Novavax, Inc., as drug products such as vaccines. Novasomes®, which provide an enhanced immunological effect, are further described in U.S. Pat. No. 4,911,928, which is incorporated herein by reference.

The invention provides a method for detecting humoral immunity to influenza virus infection in a vertebrate by providing a test reagent including an effective antibody-detecting amount of influenza virus protein having at least one conformational epitope of an influenza virus macromolecular structure. The test reagent is contacted with a sample of bodily fluid from a vertebrate to be examined for influenza virus infection. Influenza virus specific antibodies contained in the sample are allowed to bind to the conformational epitope of an influenza virus macromolecular structure to form antigen-antibody complexes. The complexes are separated from unbound complexes and contacted with a detectably labeled immunoglobulin-binding agent. The amount of the detectably labeled immunoglobulin-binding agent that is bound to the complexes is determined.

Influenza virus may be detected in a specimen from an animal or human suspected of being infected with the virus by providing antibodies, which have a detectable signal producing label, or are attached to a detectably labeled reagent, having specificity to at least one conformational epitope of the particle of the influenza virus. The specimen is contacted with antibodies and the antibodies are allowed to bind to the influenza virus. The presence of influenza virus in the specimen is determined by means of the detectable label.

The invention provides methods for treatment, prevention, and generating a protective immune response by administering to a vertebrate an effective amount of the composition of the invention.

Alternatively, the influenza VLP drug substance may be formulated as laboratory reagents used for influenza virus structure studies and clinical diagnostic assays. The invention also provides a kit for treating influenza virus by administering an effective amount of a composition of the invention and directions for use.

BRIEF DESCRIPTION OF THE DRAWINGS

FIG. 1 depicts the nucleotide sequence of avian influenza A/Hong Kong/1073/99 (H9N2) virus neuraminidase (NA) gene (SEQ ID NO:1).

FIG. 2 depicts the nucleotide sequence of avian influenza A/Hong Kong/1073/99 (H9N2) virus hemagglutinin (HA) gene (SEQ ID NO:2).

FIG. 3 depicts the nucleotide sequence of avian influenza A/Hong Kong/1073/99 (H9N2) virus matrix protein M1 (M1) gene (SEQ ID NO:3).

FIG. 4 depicts the transfer vectors for construction of recombinant baculoviruses for expression of avian influenza A/Hong Kong/1073/99 (H9N2) HA, NA, and M1 proteins.

FIG. 12A depicts sera from BALB/c mice immunized with recombinant VLPs comprised of HA, NA, and M1 proteins from avian influenza virus type A/H9N2/Hong Kong/1073/99. FIG. 12B depicts sera from New Zealand white rabbits immunized with inactivated avian influenza virus type A H9N2 were reacted with Western blots containing inactivated avian influenza virus type A H9N2 (lanes 1 and 3) or cold-adapted avian influenza virus type A H9N2 (lanes 2 and 4).

DETAILED DESCRIPTION OF THE INVENTION

Figure 4A:
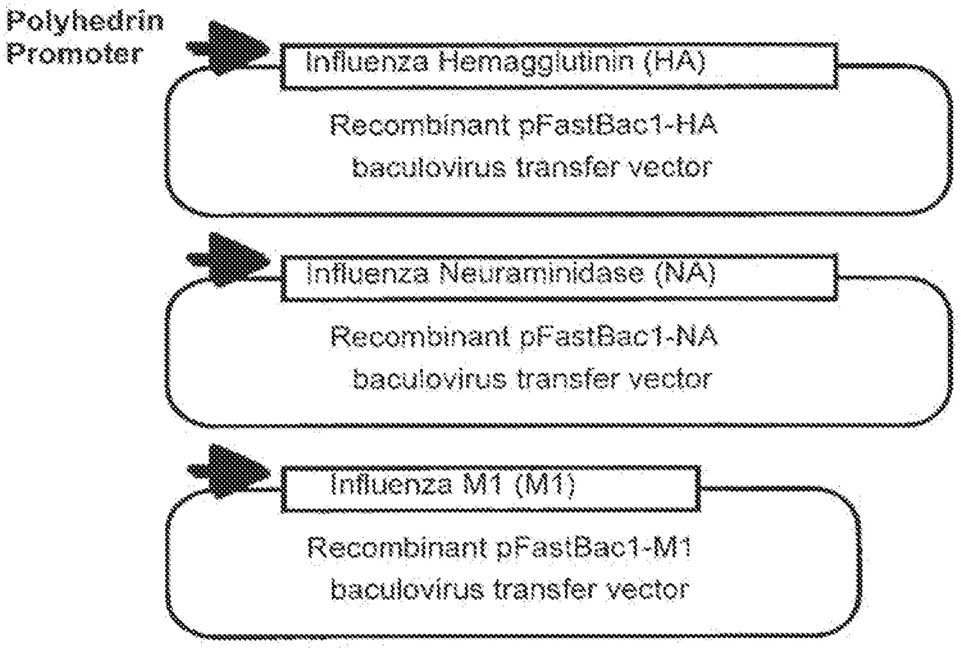
FIG. 4A depicts a transfer vector for expression of individual genes and FIG. 4B depicts the transfer vector for multi-expression of the genes.

As used herein, the term "baculovius," also known as baculoviridae, refers to a family of enveloped DNA viruses of arthropods, members of which may be used as expression vectors for producing recombinant proteins in insert cell cultures. The virion contains one or more rod-shaped nucleocapsids containing a molecule of circular supercoiled double-stranded DNA ($M_r$ $54\times10^6$-$154\times10^6$). The virus used as a vector is generally *Autographa californica* nuclear polyhedrosis virus (NVP). Expression of introduced genes is under the control of the strong promoter that normally regulates expression of the polyhedron protein component of the large nuclear inclusion in which the viruses are embedded in the infected cells.

As used herein, the term "derived from" refers to the origin or source, and may include naturally occurring, recombinant, unpurified, or purified molecules. The proteins and molecules of the present invention may be derived from influenza or non-influenza molecules.

As used herein the term "first" influenza virus protein, i.e., a first influenza virus M1 protein, refers to a protein, such as M1, HA, NA, and M2, that is derived from a particular strain of influenza virus. The strain or type of the first influenza virus differs from the strain or type of the second influenza virus protein. Thus, "second" influenza virus protein, i.e., the second influenza virus M1 protein, refers to a protein, such as M1, HA, NA, and M2, that is derived from a second strain of influenza virus, which is a different strain or type than the first influenza virus protein.

As used herein, the term "hemagglutinin activity" refers to the ability of HA-containing proteins, VLPs, or portions thereof to bind and agglutinate red blood cells (erythrocytes).

As used herein, the term "neuraminidase activity" refers to the enzymatic activity of NA-containing proteins, VLPs, or portions thereof to cleave sialic acid residues from substrates including proteins such as fetuin.

As used herein, the term "heterotypic" refers to one or more different types or strains of virus.

As used herein, the term "homotypic" refers to one type or strain of virus.

As used herein, the term "macromolecular protein structure" refers to the construction or arrangement of one or more proteins.

As used herein, the term "multivalent" vaccine refers to a vaccine against multiple types or strains of influenza virus.

As used herein, the term "non-influenza" refers to a protein or molecule that is not derived from influenza virus.

As used herein, the term "vaccine" refers to a preparation of dead or weakened pathogens, or of derived antigenic determinants, that is used to induce formation of antibodies or immunity against the pathogen. A vaccine given to provide immunity to the disease, for example, influenza, which is caused by influenza viruses. The present invention provides vaccine compositions that are immunogenic and provide protection.

Influenza remains a pervasive public health concern despite the availability of specific inactivated virus vaccines that are 60-80% effective under optimal conditions. When these vaccines are effective, illness is usually averted by preventing viral infection. Vaccine failure can occur as a result of accumulated antigenic differences (antigenic shift and antigenic drift). For example, avian influenza virus type A H9N2 co-circulated with human influenza virus type A Sydney/97 H3N2 in pigs and led to genetic reassortment and emergence of new strains of human influenza virus with pandemic potential (Peiris et al., 2001). In the event of such antigenic shift, it is unlikely that current vaccines would provide adequate protection.

Another reason for the paucity of influenza vaccine programs is the relatively short persistence of immunity elicited by the current vaccines. Further inadequacy of influenza control measures reflects restricted use of current vaccines because of vaccine reactogenicity and side effects in young children, elderly, and people with allergies to components of eggs, which are used in manufacturing of commercially licensed inactivated virus influenza vaccines.

Additionally, inactivated influenza virus vaccines often lack or contain altered HA and NA conformational epitopes, which elicit neutralizing antibodies and play a major role in protection against disease. Thus, inactivated viral vaccines, as well as some recombinant monomeric influenza subunit protein vaccines, deliver inadequate protection. On the other hand, macromolecular protein structures, such as capsomers, subviral particles, and/or VLPs, include multiple copies of native proteins exhibiting conformational epitopes, which are advantageous for optimal vaccine immunogenicity.

The present invention describes the cloning of avian influenza A/Hong Kong/1073/99 (H9N2) virus HA, NA, and M1 genes into a single baculovirus expression vector alone or in tandem and production of influenza vaccine candidates or reagents comprised of recombinant influenza structural proteins that self-assemble into functional and immunogenic homotypic macromolecular protein structures, including subviral influenza particles and influenza VLP, in baculovirus-infected insect cells.

The present invention further features the cloning of human influenza A/Sydney/5/94 (H3N2) virus HA, NA, M1, M2, and NP genes into baculovirus expression vectors and production influenza vaccine candidates or reagents comprised of influenza structural proteins that self-assemble into functional and immunogenic homotypic macromolecular protein structures, including subviral influenza particles and influenza VLP, in baculovirus-infected insect cells.

In addition, the instant invention describes the cloning of the HA gene of human influenza A/Sydney/5/94 (H3N2) virus and the HA, NA, and M1 genes of avian influenza A/Hong Kong/1073/99 (H9N2) into a single baculovirus expression vector in tandem and production influenza vaccine candidates or reagents comprised of influenza structural proteins that self-assemble into functional and immunogenic heterotypic macromolecular protein structures, including subviral influenza particles and influenza VLP, in baculovirus-infected insect cells.

This invention is further illustrated by the following examples which should not be construed as limiting. The contents of all references, patents and published patent applications cited throughout this application, as well as the Figures and the Sequence Listing, are incorporated herein by reference.

SPECIFIC EXAMPLES

Example 1

Materials and Methods

Avian influenza A/Hong Kong/1073/99 (H9N2) virus HA, NA, and M1 genes were expressed in *Spodoptera frugiperda* cells (Sf-9S cell line; ATCC PTA-4047) using the baculovirus bacmid expression system. The HA, NA, and M1 genes were synthesized by the reverse transcription and polymerase chain reaction (PCR) using RNA isolated from avian influenza A/Hong Kong/1073/99 (H9N2) virus (FIGS. 1, 2, and 3). For reverse transcription and PCR, oligonucleotide primers specific for avian influenza A/Hong Kong/1073/99 (H9N2) virus HA, NA, and M1 genes were used (Table 1). The cDNA copies of these genes were cloned initially into the bacterial subcloning vector, pCR2.1TOPO. From the resulting three pCR2.1TOPO-based plasmids, the HA, NA, and M1 genes were inserted downstream of the AcMNPV polyhedrin promoters in the baculovirus transfer vector, pFastBac1 (InVitrogen), resulting in three pFastBac1-based plasmids: pHA, pNA, and pM1 expressing these influenza virus genes, respectively. Then, a single pFastBac1-based plasmid pHAM was constructed encoding both the HA and M1 genes, each downstream from a separate polyhedrin promoter (FIG. 4). The nucleotide sequence of the NA gene with the adjacent 5'- and 3'-regions within the pNA plasmid was determined (SEQ ID NO:1) (FIG. 1). At the same time, the nucleotide sequences of the HA and M1 genes with the adjacent regions were also determined using the pHAM plasmid (SEQ ID NOS:2 and 3) (FIGS. 2 and 3).

Finally, a restriction DNA fragment from the pHAM plasmid that encoded both the HA and M1 expression cassettes was cloned into the pNA plasmid. This resulted in the plasmid pNAHAM encoding avian influenza A/Hong Kong/1073/99 (H9N2) virus HA, NA, and M1 genes (FIG. 4).

Plasmid pNAHAM was used to construct a recombinant baculovirus containing influenza virus NA, HA, and M1 genes integrated into the genome, each downstream from a separate baculovirus polyhedrin promoter. Infection of permissive Sf-9S insect cells with the resulting recombinant baculovirus resulted in co-expression of these three influenza genes in each Sf-9S cell infected with such recombinant baculovirus.

Results

Figure 5:
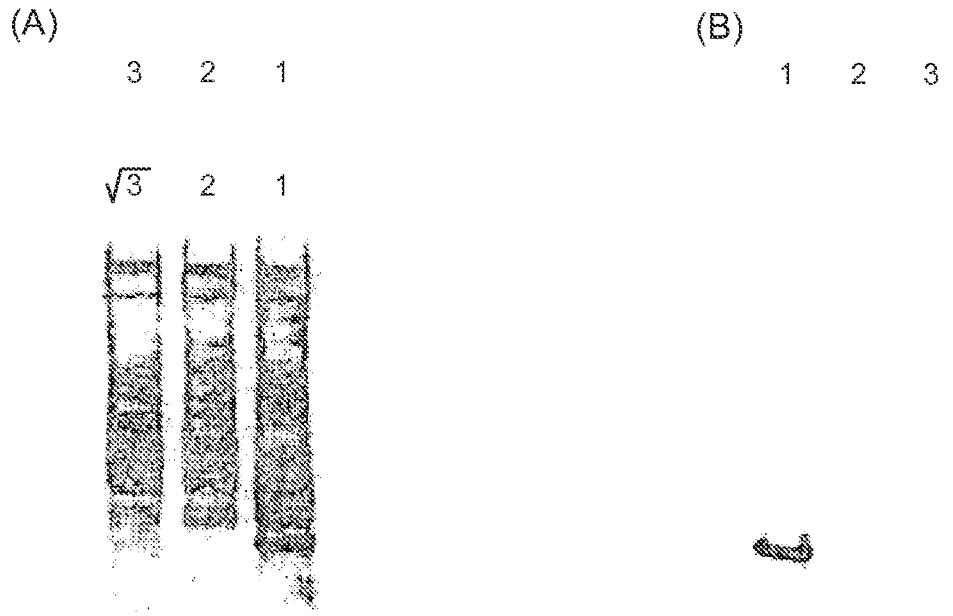
FIG. 5 depicts the expression of avian influenza A/Hong Kong/1073/99 (H9N2) virus HA, NA, and M1 proteins in Sf-9S cells.

The expression products in infected Sf-9S cells were characterized at 72 hr postinfection (p.i.) by SDS-PAGE analysis, Coomassie blue protein staining, and Western immunoblot analysis using HA- and M1-specific antibodies (FIG. 5). Western immunoblot analysis was carried out using rabbit antibody raised against influenza virus type A/Hong Kong/1073/99 (H9N2) (CDC, Atlanta, Ga., USA), or mouse monoclonal antibody to influenza M1 protein (Serotec, UK). The HA, NA, and M1 proteins of the expected molecular weights (64 kd, 60 kd, and 31 kd, respectively) were detected by Western immunoblot analysis. Compared to the amount of HA protein detected in this assay, the NA protein showed lower reactivity with rabbit serum to influenza A/Hong Kong/1073/99 (H9N2) virus. Explanations for the amount of detectable NA protein included lower expression levels of the NA protein from Sf-9S cells infected with recombinant baculovirus as compared to the HA protein, lower reactivity of the NA with this serum under denaturing conditions in the Western immunoblot assay (due to the elimination of important NA epitopes during gel electrophoresis of membrane binding), lower NA-antibody avidity as compared to HA-antibody, or a lower abundance of NA-antibodies in the serum.

The culture medium from the Sf-9S cells infected with recombinant baculovirus expressing A/Hong Kong/1073/99 (H9N2) HA, NA, and M1 proteins was also probed for influenza proteins. The clarified culture supernatants were subjected to ultracentrifugation at 27,000 rpm in order to concentrate high-molecular protein complexes of influenza virus, such as subviral particles, VLP, complexes of VLP, and possibly, other self-assembled particulates comprised of influenza HA, NA, and M1 proteins. Pelleted protein products were resuspended in phosphate-buffered saline (PBS, pH 7.2) and further purified by ultracentrifugation on discontinuous 20-60% sucrose step gradients. Fractions from the sucrose gradients were collected and analyzed by SDS-PAGE analysis, Western immunoblot analysis, and electron microscopy.

Figure 6:
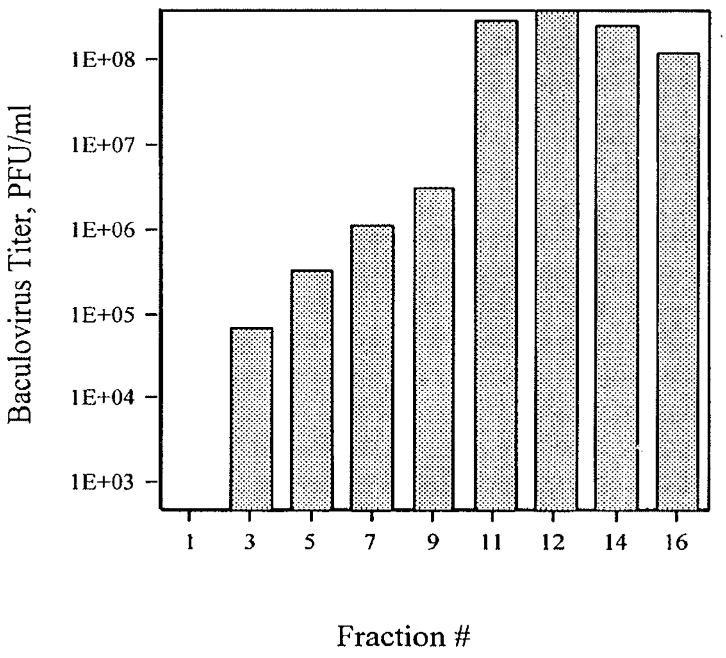
FIG. 6 depicts the purification of avian influenza A/Hong Kong/1073/99 (H9N2) VLPs by the sucrose density gradient method.

Influenza HA and M1 proteins of the expected molecular weights were detected in multiple sucrose density gradient fractions by Coomassie blue staining and Western immunoblot analysis (FIG. 6). This suggested that influenza viral proteins from infected Sf-9S cells are aggregated in complexes of high-molecular weight, such as capsomers, subviral particles, VLP, and/or VLP complexes. The NA proteins, although inconsistently detected by Coomassie blue staining and Western immunoblot analysis, which was likely due to the inability of the rabbit anti-influenza serum to recognize denatured NA protein in the Western immunoblot assay, were consistently detected in neuraminidase enzyme activity assay (FIG. 10).

Figure 7:
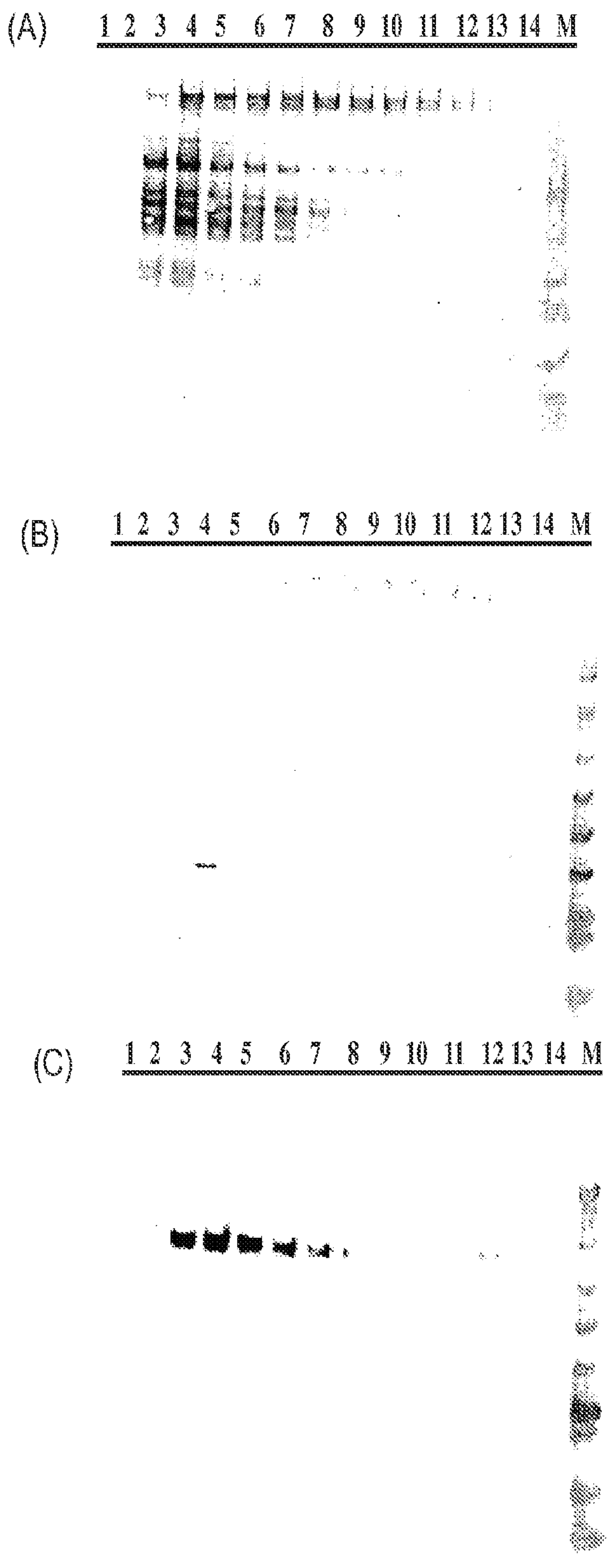
FIG. 7 depicts the detection of influenza virus protein by gel filtration chromatography. The antibodies used in the Western blot analyses are as follows: (A) rabbit anti-H9N2; (b) murine anti-M1 mAb; and (C) murine anti-BACgp64.

The presence of high-molecular VLPs was confirmed by gel filtration chromatography. An aliquot from sucrose density gradient fractions containing influenza viral proteins was loaded onto a Sepharose CL-4B column for fractionation based on mass. The column was calibrated with dextran blue 2000, dextran yellow, and vitamin B12 (Amersham Pharmacia) with apparent molecular weights of 2,000,000; 20,000; and 1,357 daltons, respectively, and the void volume of the column was determined. As expected, high-molecular influenza viral proteins migrated in the void volume of the column, which was characteristic of macromolecular proteins, such as virus particles. Fractions were analyzed by Western immunoblot analysis to detect influenza and baculovirus proteins. For example, M1 proteins were detected in the void volume fractions, which also contained baculovirus proteins (FIG. 7).

Figure 8:
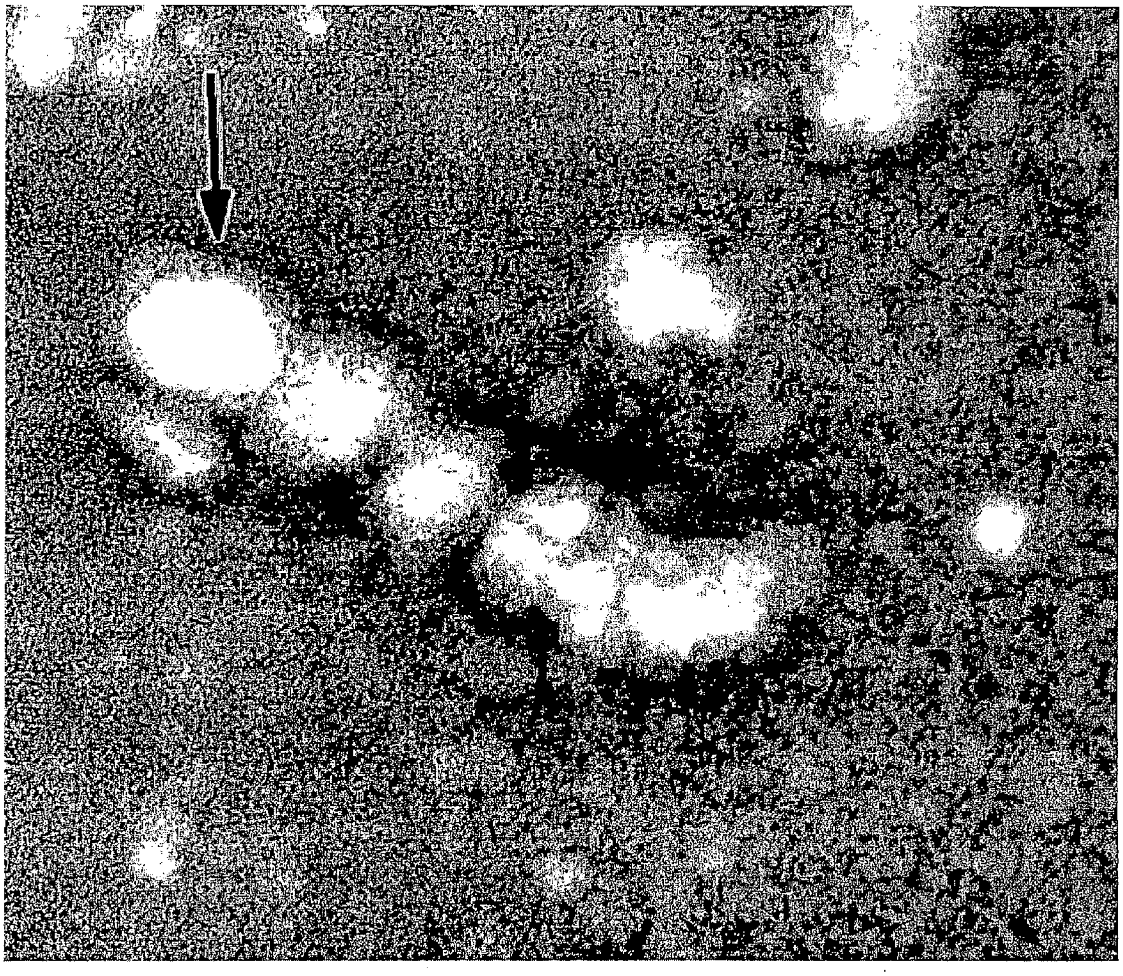
FIG. 8 depicts the detection of avian influenza A/Hong Kong/1073/99 (H9N2) proteins including subviral particles, VLP, and VLP complexes, by electron microscopy.

The morphology of influenza VLPs and proteins in sucrose gradient fractions was elucidated by electron microscopy. For negative-staining electron microscopy, influenza proteins from two sucrose density gradient fractions were fixed with 2% glutaraldehyde in PBS, pH 7.2. Electron microscopic examination of negatively-stained samples revealed the presence of macromolecular protein complexes or VLPs in both fractions. These VLPs displayed different sizes including diameters of approximately 60 and 80 nm and morphologies (spheres). Larger complexes of both types of particles were also detected, as well as rod-shaped particles (FIG. 8). All observed macromolecular structures had spikes (peplomers) on their surfaces, which is characteristic of influenza viruses. Since the size and appearance of 80 nm particles was similar to particles of wild type influenza virus, these structures likely represented VLPs, which have distinct similarities to wild type influenza virions, including similar particle geometry, architecture, triangulation number, symmetry, and other characteristics. The smaller particles of approximately 60 nm may represent subviral particles that differ from VLPs both morphologically and structurally. Similar phenomenon of recombinant macromolecular proteins of different sizes and morphologies was also reported for other viruses. For example, recombinant core antigen (HBcAg) of hepatitis B virus forms particles of different sizes, which have different architecture and triangulation number T=4 and T=3, respectively (Crowther et al., 1994).

Figure 9:
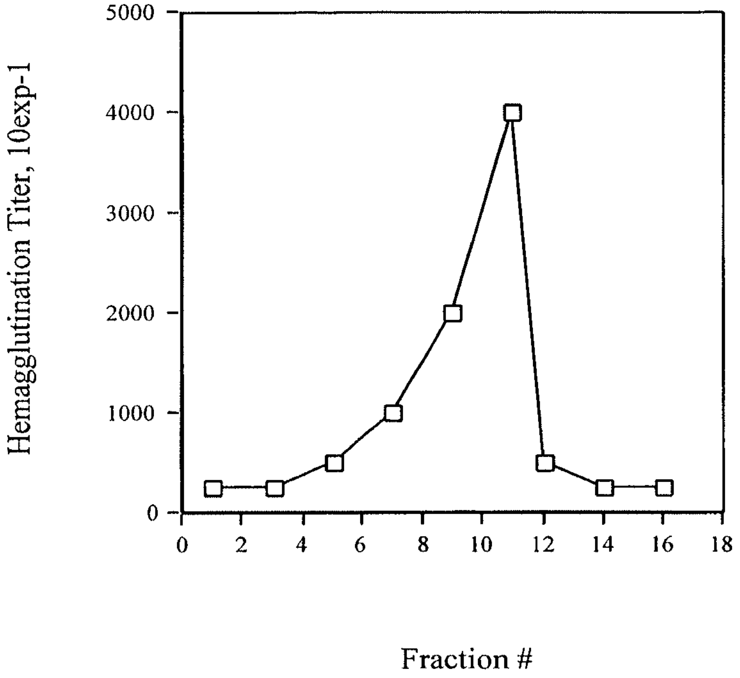
FIG. 9 depicts the hemagglutination activity of purified avian influenza A/Hong Kong/1073/99 (H9N2) VLPs.
Figure 10:
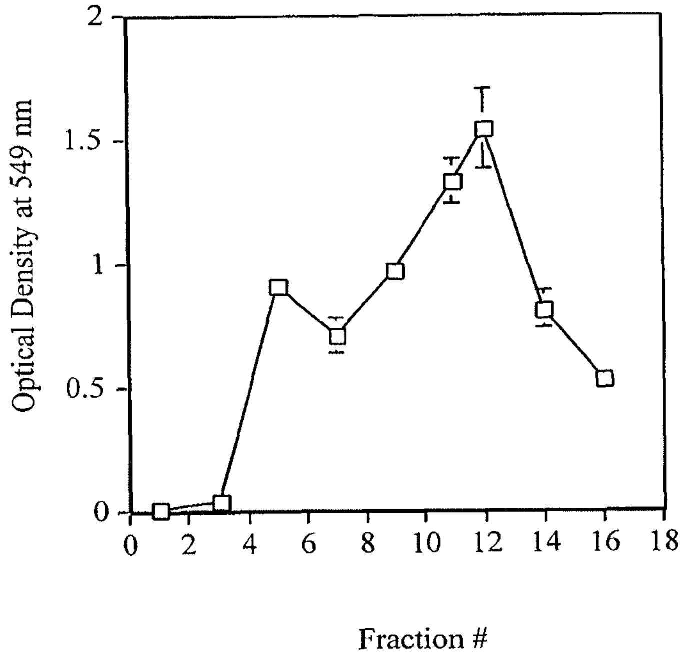
FIG. 10 depicts the neuraminidase activity of purified avian influenza A/Hong Kong/1073/99 (H9N2) VLPs.

To characterize the functional properties of the purified influenza A/Hong Kong/1073/99 (H9N2) VLPs, samples were tested in a hemagglutination assay (FIG. 9) and a neuraminidase enzyme assay (FIG. 10). For the hemagglutination assay, 2-fold dilutions of purified influenza VLPs were mixed with 0.6% guinea pig red blood cells and incubated at 4° C. for 1 hr or 16 hr. The extent of hemagglutination was inspected visually and the highest dilution of recombinant influenza proteins capable of agglutinating red blood cells was determined and recorded (FIG. 9). Again, many fractions from the sucrose density gradient exhibited hemagglutination activity, suggesting that multiple macromolecular and monomeric forms of influenza proteins were present. The highest titer detected was 1:4000. In a control experiment, wild-type influenza A/Shangdong virus demonstrated a titer of 1:2000. The hemagglutination assay revealed that the recombinant VLPs consisting of influenza A/Hong Kong/1073/99 (H9N2) virus HA, NA, and M1 proteins were functionally active. This suggested that the assembly, conformation, and folding of the HA subunit proteins within the VLPs were similar or identical to that of the wild type influenza virus.

Additionally, a neuraminidase enzyme assay was performed on samples of purified H9N2 VLPs. The amount of neuraminidase activity in sucrose density gradient fractions was determined using fetuin as a substrate. In the neuraminidase assay, the neuraminidase cleaved sialic acid from substrate molecules to release sialic acid for measurement. Arsenite reagent was added to stop enzyme activity. The amount of sialic acid liberated was determined chemically with thiobarbituric acid that produces a pink color that was proportional to the amount of free sialic acid. The amount of color (chromophor) was measured spectrophotometrically at wavelength 549 nm. Using this method, neuraminidase activity was demonstrated in sucrose gradient fractions containing influenza VLPs (FIG. 10). As expected, the activity was observed in several fractions, with two peak fractions. As a positive control, wild type influenza virus was used. The wild type influenza virus exhibited neuraminidase enzyme activity comparable to that of purified influenza VLPs. These findings corroborated the HA results with regard to protein conformation and suggested that purified VLPs of influenza A/Hong Kong/1073/99 (H9N2) virus were functionally similar to wild type influenza virus.

The results from the above analyses and assays indicated that expression of influenza A/Hong Kong/1073/99 (H9N2) HA, NA, and M1 proteins was sufficient for the self-assembly and transport of functional VLPs from baculovirus-infected insect cells. Since these influenza VLPs represented self-assembled influenza structural proteins and demonstrated functional and biochemical properties similar to those of wild type influenza virus, these influenza VLPs conserved important structural conformations including surface epitopes necessary for effective influenza vaccines.

Example 2

RT-PCR Cloning of Avian Influenza A/Hong Kong/1073/99 Viral Genes

It is an object of the present invention to provide synthetic nucleic acid sequences capable of directing production of recombinant influenza virus proteins. Such synthetic nucleic acid sequences were obtained by reverse transcription and polymerase chain reaction (PCR) methods using influenza virus natural genomic RNA isolated from the virus. For the purpose of this application, nucleic acid sequence refers to RNA, DNA, cDNA or any synthetic variant thereof which encodes the protein.

Avian influenza A/Hong Kong/1073/99 (H9N2) virus was provided by Dr. K. Subbarao (Centers for Disease Control, Atlanta, Ga., USA). Viral genomic RNA was isolated by the acid phenol RNA extraction method under Biosafety Level 3 (BSL3) containment conditions at CDC using Trizol LS reagent (Invitrogen, Carlsbad, Calif. USA). cDNA molecules of the viral RNAs were obtained by reverse transcription using MuLV reverse transcriptase (InVitrogen) and PCR using oligonucleotide primers specific for HA, NA, and M1 proteins and Taq I DNA polymerase (InVitrogen) (Table 1). The PCR fragments were cloned into the bacterial subcloning vector, pCR2.1TOPO (InVitrogen), between Eco RI sites that resulted in three recombinant plasmids, containing the HA, NA, and M1 cDNA clones.

Example 3

RT-PCR Cloning of Human Influenza A/Sydney/5/94 (H3N2) Viral Genes

Influenza A/Sydney/5/94 (H3N2) virus was obtained from Dr. M. Massare (Novavax, Inc., Rockville, Md.). Viral genomic RNA was isolated by the RNA acid phenol extraction method under BSL2 containment conditions at Novavax, Inc. using Trizol LS reagent (Invitrogen). cDNA molecules of the viral RNAs were obtained by reverse transcription and PCR using oligonucleotide primers specific for HA, NA, M1, M2, and NP proteins (Table 2). The PCR fragments were cloned into the bacterial subcloning vector, pCR2.1TOPO, between Eco RI sites that resulted in five recombinant plasmids, containing the HA, NA, M1, M2, and NP cDNA clones.

Example 4

Cloning of Avian Influenza A/Hong Kong/1073/99 Viral cDNAs into Baculovirus Transfer Vectors From the pCR2.1TOPO-based plasmids, the HA, NA, or M1 genes were subcloned into pFastBac1 baculovirus transfer vector (InVitrogen) within the polyhedron locus and Tn7 att sites and downstream of the baculovirus polyhedrin promoter and upstream of the polyadenylation signal sequence. The viral genes were ligated with T4 DNA ligase. For the HA gene, a Bam HI-Kpn I DNA fragment from pCR2.1TOPO-HA was inserted into Bam HI-Kpn I digested pFastBac1 plasmid DNA. For the NA gene, an Eco RI DNA fragment from pCR2.1TOPO-NA was inserted into Eco RI digested pFastBac1 plasmid DNA. For the M1 gene, an Eco RI DNA fragment from pCR2.1TOPO-M1 was inserted into Eco RI digested pFastBac1 plasmid DNA. Competent *E. coli* DH5α_bacteria (InVitrogen) were transformed with these DNA ligation reactions, transformed colonies resulted, and bacterial clones isolated. The resulting pFastBac1-based plasmids, pFastBac1-HA, pFastBac1-NA, and pFastBac1-M1 were characterized by restriction enzyme mapping on agarose gels (FIG. 4A). The nucleotide sequences as shown on FIGS. 1-3 of the cloned genes were determined by automated DNA sequencing. DNA sequence analysis showed that the cloned influenza HA, NA, and M1 genes were identical to the nucleotide sequences for these genes as published previously [NA, HA, and M1 genes of influenza A/Hong Kong/1073/99 (H9N2) (GenBank accession numbers AJ404629, AJ404626, and AJ278646, respectively)].

Example 5

Cloning of Human Influenza A/Sydney/5/94 Viral cDNAs into Baculovirus Transfer Vectors From the pCR2.1TOPO-based plasmids, the HA, NA, M1, M2, and NP genes were subcloned into pFastBac1 baculovirus transfer vector within the polyhedron locus and Tn7 att sites and downstream of the baculovirus polyhedrin promoter and upstream of the polyadenylation signal sequence. The viral genes were ligated with T4 DNA ligase. For the HA gene, a Bam HI-Kpn I DNA fragment from pCR2.1TOPO-hHA3 was inserted into Bam HI-Kpn I digested pFastBac1 plasmid DNA. For the NA gene, an Eco RI DNA fragment from pCR2.1TOPO-hNA was inserted into Eco RI digested pFastBac1 plasmid DNA. For the M1 gene, an Eco RI DNA fragment from pCR2.1TOPO-hM1 was inserted into Eco RI digested pFastBac1 plasmid DNA.

For the M2 gene, an Eco RI DNA fragment from pCR2.1TOPO-hM2 was inserted into Eco RI digested pFastBac1 plasmid DNA. For the NP gene, an Eco RI DNA fragment from pCR2.1TOPO-hNP was inserted into Eco RI digested pFastBac1 plasmid DNA. Competent *E. coli* DH5α_bacteria were transformed with these DNA ligation reactions, transformed colonies resulted, and bacterial clones isolated. The resulting pFastBac1-based plasmids, pFastBac1-hHA3, pFastBac1-hNA2, pFastBac1-hM1, pFASTBAC1-hM2, and pFASTBAC1-hNP were characterized by restriction enzyme mapping on agarose gels. The nucleotide sequences of the cloned genes were determined by automated DNA sequencing. DNA sequence analysis showed that the cloned influenza HA, NA, M1, M2, and NP genes were identical to the nucleotide sequences for these genes as published previously.

Example 6

Construction of Multigenic Baculovirus Transfer Vectors Encoding Multiple Avian Influenza A/Hong Kong/1073/99 Viral Genes In order to construct pFastBac1-based bacmid transfer vectors expressing multiple influenza A/Hong Kong/1073/99 (H9N2) virus genes, initially a Sna BI-Hpa I DNA fragment from pFastBac1-M1 plasmid containing the M1 gene was cloned into Hpa I site of pFastBac1-HA. This resulted in pFastBac1-HAM plasmid encoding both HA and M1 genes within independent expression cassettes and expressed under the control of separate polyhedrin promoters.

Figure 4B:
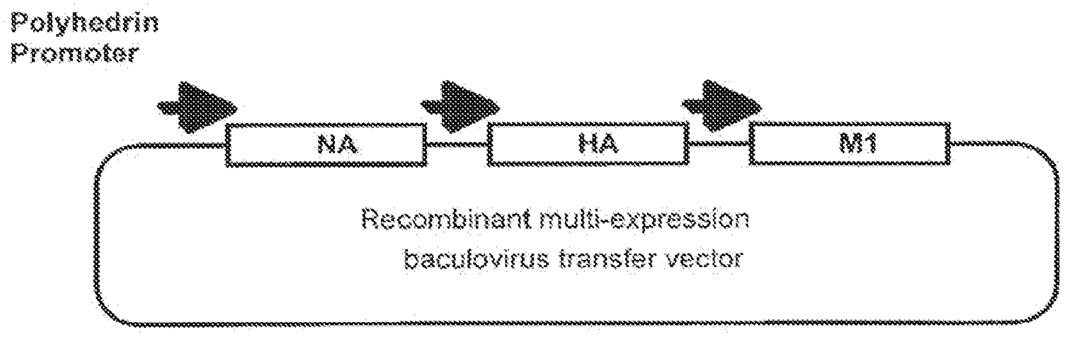

Finally, a Sna BI-Avr II DNA fragment from pFastBac1-HAM containing the HA and M1 expression cassettes, was transferred into Hpa I-Avr II digested pFastBac1-NA plasmid DNA. This resulted in the plasmid pFastBac1-NAHAM encoding three independent expression cassettes for expression of influenza HA, NA, and M1 genes and expressed under the control of separate polyhedrin promoters (FIG. 4B).

In another example, the H3 gene from pFASTBAC1-hHA3 (see Example 5) was cloned into pFASTBAC1-NAHAM as a fourth influenza viral gene for the expression and production of heterotypic influenza VLPs.

Example 7

Generation of Multigenic Recombinant Baculovirus Encoding NA, HA, and M1 Genes of Avian Influenza A/Hong Kong/1073/99 Virus in Insect Cells The resulting multigenic bacmid transfer vector pFastBac1-NAHAM was used to generate a multigenic recombinant baculovirus encoding avian influenza A/Hong Kong/1073/99 (H9N2) HA, NA, and M1 genes for expression in insect cells. Recombinant bacmid DNAs were produced by site-specific recombination at polyhedrin and Tn7 att DNA sequences between pFastBac1-NAHAM DNA and the AcMNPC baculovirus genome harbored in competent *E. coli* DH10BAC cells (InVitrogen) (FIG. 4B). Recombinant bacmid DNA was isolated by the mini-prep plasmid DNA method and transfected into Sf-9s cells using the cationic lipid CELLFECTIN (InVitrogen). Following transfection, recombinant baculoviruses were isolated, plaque purified, and amplified in Sf-9S insect cells. Virus stocks were prepared in Sf-9S insect cells and characterized for expression of avian influenza viral HA, NA, and M1 gene products. The resulting recombinant baculovirus was designated bNAHAM-H9N2.

Example 8

Expression of Recombinant Avian Influenza a/Hong Kong/1073/99 Proteins in Insect Cells Sf-9S insect cells maintained as suspension cultures in shaker flasks at 28° C. in serum-free medium (HyQ SFM, HyClone, Ogden, Utah) were infected at a cell density of $2\times10^6$ cells/ml with the recombinant baculovirus, bNAHAM-H9N2, at a Multiplicity of infection (MOI) of 3 pfu/cell. The virus infection proceeded for 72 hrs. to allow expression of influenza proteins. Expression of avian influenza A/Hong Kong/1073/99 (H9N2) HA and M1 proteins in infected insect cells was confirmed by SDS-PAGE and Western immunoblot analyses. SDS-PAGE analysis was performed on 4-12% linear gradient NuPAGE gels (Invitrogen) under reduced and denaturing conditions. Primary antibodies in Western immunoblot analysis were polyclonal rabbit antiserum raised against avian influenza A/Hong Kong/1073/99 (H9N2) obtained from CDC and monoclonal murine antiserum to influenza M1 protein (Serotec, UK). Secondary antibodies for Western immunoblot analysis were alkaline phosphatase conjugated goat IgG antisera raised against rabbit or mouse IgG (H+L) (Kirkegaard and Perry Laboratories, Gaithersburg, Md., USA). Results of these analyses (FIG. 5) indicated that the HA and M1 proteins were expressed in the baculovirus-infected insect cells.

Example 9

Purification of Recombinant Avian Influenza H9N2 Virus-Like Particles and Macromolecular Protein Complexes Culture supernatants (200 ml) from Sf-9S insect cells infected with the recombinant baculovirus bNAHAM-H9N2 that expressed avian influenza A/Hong Kong/1073/99 (H9N2) HA, NA, and M1 gene products were harvested by low speed centrifugation. Culture supernatants were clarified by centrifugation in a Sorval RC-5B superspeed centrifuge for 1 hr at 10,000×g and 4° C. using a GS-3 rotor. Virus and VLPs were isolated from clarified culture supernatants by centrifugation in a Sorval OTD-65 ultracentrifuge for 3 hr at 27,000 rpm and 4° C. using a Sorval TH-641 swinging bucket rotor. The virus pellet was resuspended in 1 ml of PBS (pH 7.2), loaded onto a 20-60% (w/v) discontinuous sucrose step gradient, and resolved by centrifugation in a Sorval OTD-65 ultracentrifuge for 16 hr at 27,000 rpm and 4° C. using a Sorval TH-641 rotor. Fractions (0.5 ml) were collected from the top of the sucrose gradient.

Influenza proteins in the sucrose gradient fractions were analyzed by SDS-PAGE and Western immunoblot analyses as described above in Example 6. The HA and M1 proteins were found in the same sucrose gradient fractions (FIG. 6) as shown by Western blot analysis and suggested that the HA and M1 proteins were associated as macromolecular protein complexes. Also the HA and M1 proteins were found in fractions throughout the sucrose gradient suggesting that these recombinant viral proteins were associated with macromolecular protein complexes of different densities and compositions.

Example 10

Analysis of Recombinant Avian Influenza H9N2 VLPs and Proteins by Gel Filtration Chromatography Protein macromolecules such as VLPs and monomeric proteins migrate differently on gel filtration or size exclusion chromatographic columns based on their mass size and shape. To determine whether the recombinant influenza proteins from sucrose gradient fractions were monomeric proteins or macromolecular protein complexes such as VLPs, a chromatography column (7 mm×140 mm) with a resin bed volume of 14 ml of Sepharose CL-4B (Amersham) was prepared. The size exclusion column was equilibrated with PBS and calibrated with Dextran Blue 2000, Dextran Yellow, and Vitamin B12 (Amersham Pharmacia) with apparent molecular weights of 2,000,000; 20,000; and 1,357, respectively, to ascertain the column void volume. Dextran Blue 2000 eluted from the column in the void volume (6 ml fraction). As expected, the recombinant influenza protein complexes eluted from the column in the void volume (6 ml fraction) also. This result was characteristic of a high molecular weight macromolecular protein complex such as VLPs. Viral proteins in the column fractions were detected by Western immunoblot analysis as described above in Example 6. The M1 proteins were detected in the void volume fractions (FIG. 7). As expected baculovirus proteins were also in the void volume.

Example 11

Electron Microscopy of Recombinant Influenza VLPs

To determine whether the macromolecular protein complexes isolated on sucrose gradients and containing recombinant avian influenza proteins had morphologies similar to influenza virions, electron microscopic examination of negatively stained samples was performed. Recombinant avian influenza A/Hong Kong/1073/99 (H9N2) protein complexes were concentrated and purified from culture supernatants by ultracentrifugation on discontinuous sucrose gradients as described in Example 7. Aliquots of the sucrose gradient fractions were treated with a 2% glutaraldehyde in PBS, pH7.2, absorbed onto fresh discharged plastic/carbon-coated grids, and washed with distilled water. The samples were stained with 2% sodium phosphotungstate, pH 6.5, and observed using a transmission electron microscope (Philips). Electron micrographs of negatively-stained samples of recombinant avian influenza H9N2 protein complexes from two sucrose gradient fractions showed spherical and rod-shaped particles (FIG. 8) from two sucrose gradient fractions. The particles had different sizes (60 and 80 nm) and morphologies. Larger complexes of both types of particles were also detected, as well as rod-shaped particles (FIG. 8). All observed protein complex structures exhibited spike like surface projections resembling influenza virus HA and NA peplomers. Since the size and appearance of the 80 nm particles was similar to that of wild type influenza virus particles, these structures likely represented enveloped influenza VLPs. The smaller particles of approximately 60 nm probably represented subviral particles that differed from the above VLPs both morphologically and structurally.

Example 12

Analysis of Functional Characteristics of Influenza Proteins by Hemagglutination Assay To determine whether the purified influenza VLPs and proteins possessed functional activities, such as hemagglutination and neuraminidase activity, which were characteristic for influenza virus, the purified influenza VLPs and proteins were tested in hemagglutination and neuraminidase assays.

For the hemagglutination assay, a series of 2-fold dilutions of sucrose gradient fractions containing influenza VLPs or positive control wild type influenza virus type A were prepared. Then they were mixed with 0.6% guinea pig red blood cells in PBS (pH 7.2) and incubated at 4° C. for 1 to 16 hr. As a negative control, PBS was used. The extent of hemagglutination was determined visually, and the highest dilution of fraction capable of agglutinating guinea pig red blood cells was determined (FIG. 9). The highest hemagglutination titer observed for the purified influenza VLPs and proteins was 1:4000, which was higher than the titer shown by the wild type influenza control, which was 1:2000.

Example 13

Analysis of Functional Characteristics of Influenza Proteins by Neuraminidase Assay The amount of neuraminidase activity in influenza VLP-containing sucrose gradient fractions was determined by the neuraminidase assay. In this assay the NA (an enzyme) acted on the substrate (fetuin) and released sialic acid. Arsenite reagent was added to stop enzyme activity. The amount of sialic acid liberated was determined chemically with the thiobarbituric acid that produced a pink color in proportion to free sialic acid. The amount of color (chromophor) was measured in a spectrophotometer at wavelength 594 nm. The data, as depicted in FIG. 8, showed that a significant amount of sialic acid was produced by VLP-containing fractions of the sucrose gradients and that these fractions corresponded to those fractions exhibiting hemagglutination activity.

Example 13

Figure 11:
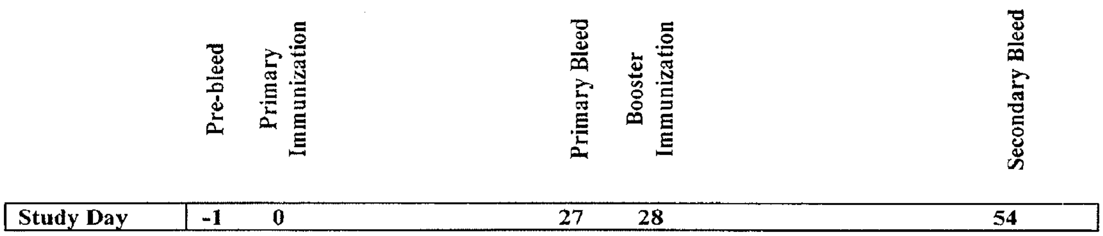
FIG. 11 depicts the immunization and bleed schedule for the immunogenicity study of recombinant influenza with purified avian influenza A/Hong Kong/1073/99 (H9N2) VLPs in mice.

Immunization of BALB/c Mice with Functional Homotypic Recombinant Influenza H9N2 VLPs The immunogenicity of the recombinant influenza VLPs was ascertained by immunization of mice followed by Western blot analysis of immune sera. Recombinant VLPs (1 μg/injection) comprised of viral HA, NA, and M1 proteins from avian influenza virus type A/Honk Kong/1073/99 and purified on sucrose gradients were inoculated subcutaneously into the deltoid region of ten (10) female BALB/c mice at day 0 and day 28 (FIG. 11). PBS (pH 7.2) was administered similarly as a negative control into five (5) mice. The mice were bled from the supraorbital cavity at day-1 (pre-bleed), day 27 (primary bleed), and day 54 (secondary bleed). Sera were collected from blood samples following overnight clotting and centrifugation.

For Western blot analysis, 200 ng of inactivated avian influenza virus type A H9N2 or cold-adapted avian influenza virus type A H9N2, as well as See Blue Plus 2 pre-stained protein standards (InVitrogen), was denatured (95° C., 5 minutes) and subjected to electrophoresis under reduced conditions (10 mM β-mercaptoethanol) on 4-12% polyacrylamide gradient NuPAGE gels (InVitrogen) in MES buffer at 172 volts until the bromophenol blue tracking dye disappeared. For protein gels, the electrophoresced proteins were visualized by staining with Colloidal Coomassie Blue reagent (InVitrogen). Proteins were transferred from the gel to nitrocellulose membranes in methanol by the standard Western blot procedure. Sera from VLP-immunized mice and rabbits immunized with inactivated avian influenza virus H9N2 (positive control sera) were diluted 1:25 and 1:100, respectively, in PBS solution (pH 7.2) and used as primary antibody. Protein bound membranes, which were blocked with 5% casein, were reacted with primary antisera for 60 minutes at room temperature with constant shaking. Following washing of primary antibody membranes with phosphate buffered saline solution containing Tween 20, secondary antisera [goat anti-murine IgG-alkaline phosphatase conjugate (1:10,000) or goat anti-rabbit IgG-alkaline phosphatase conjugate (1:10,000)] were reacted 60 minutes with the membrane. Following washing of secondary antibody membranes with phosphate buffered saline solution containing Tween 20, antibody-binding proteins on the membranes were visualized by development with the chromogenic substrate such as NBT/BCIP (InVitrogen).

Figure 12:
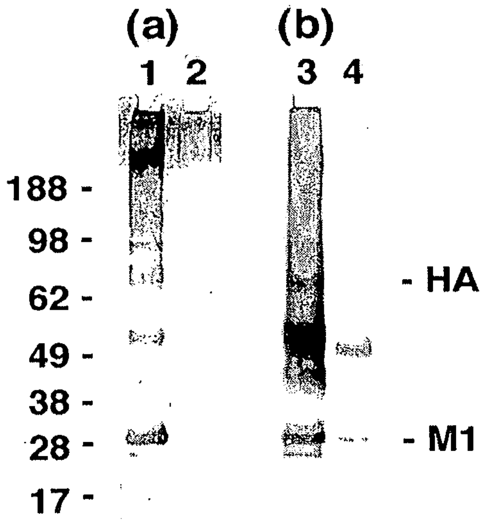
FIG. 12 depicts the results of an immunogenicity study in mice immunized with recombinant influenza H9N2 VLPs.

The results of Western blot analysis (FIG. 12) were that proteins with molecular weights similar to viral HA and M1 proteins (75 and 30 kd, respectively) bound to positive control sera (FIG. 12B) and sera from mice immunized with the recombinant influenza H9N2 VLPs (FIG. 12A). These results indicated that the recombinant influenza H9N2 VLPs alone were immunogenic in mice by this route of administration.

The following references are incorporated herein by reference:

Berglund, P., Fleeton, M. N., Smerdou, C., and Liljestrom, P. (1999). Immunization with recombinant Semliki Forest virus induces protection against influenza challenge in mice. *Vaccine* 17, 497-507.

Cox, J. C., and Coulter, A. R. (1997). Adjuvants—a classification and review of their modes of action. *Vaccine* 15, 248-256.

Crawford, J., Wilkinson, B., Vosnesensky, A., Smith, G., Garcia, M., Stone, H., and Perdue, M. L. (1999). Baculovirus-derived hemagglutinin vaccines protect against lethal influenza infections by avian H5 and H7 subtypes. *Vaccine* 17, 2265-2274.

Crowther R A, Kiselev N A, Bottcher B, Berriman J A, Borisova G P, Ose V, Pumpens P. (1994). Three-dimensional structure of hepatitis B virus core particles determined by electron cryomicroscopy. *Cell* 17, 943-50.

Gomez-Puertas, P., Mena, I., Castillo, M., Vivo, A., Perez-Pastrana, E., and Portela, A. (1999). Efficient formation of influenza virus-like particles: dependence on the expression levels of viral proteins. *J. Gen. Virol.* 80, 1635-1645.

Johansson, B. E. (1999). Immunization with influenza A virus hemagglutinin and neuraminidase produced in recombinant baculovirus results in a balanced and broadened immune response superior to conventional vaccine. *Vaccine* 17, 2073-2080.

Lakey, D. L., Treanor, J. J., Betts, B. F., Smith, G. E., Thompson, J., Sannella, E., Reed, G., Wilkinson, B. E., and Wright, P. E. (1996) Recombinant baculovirus influenza A hemagglutinin vaccines are well tolerated and immunogenic in healthy adults. *J. Infect. Dis.* 174, 838-841.

Latham, T., and Galarza, J. M. (2001). Formation of wild-type and chimeric influenza virus-like particles following simultaneous expression of only four structural proteins. *J. Virol.* 75, 6154-6165.

Mena, I., Vivo, A., Perez, E., and Portela, A (1996). Rescue of a synthetic chloramphenicol acetyltransferase RNA into influenza-like particles obtained from recombinant plasmids. *J. Virol.* 70, 5016-5024.

Murphy, B. R., and Webster, R. G. (1996). Orthomyxoviruses. In "Virology" (D. M. K. B. N. Fields, P. M. Howley, Eds.) Vol. 1, pp. 1397-1445. Lippincott-Raven, Philadelphia.

Neumann, G., Watanabe, T., and Kawaoka, Y. (2000). Plasmid-driven formation of influenza virus-like particles. *J. Virol.* 74, 547-551.

Olsen, C. W., McGregor, M. W., Dybdahl-Sissoko, N., Schram, B. R., Nelson, K. M., Lunn, D. P., Macklin, M. D., and Swain, W. F. (1997). Immunogenicity and efficacy of baculovirus-expressed and DNA-based equine influenza virus hemagglutinin vaccines in mice. *Vaccine* 15, 1149-1156.

Peiris, J. S., Guan, Y., Markwell, D., Ghose, P., Webster, R. G., and Shortridge, K. F. (2001). Cocirculation of avian H9N2 and contemporary "human" H3N2 influenza A viruses in pigs in southwestern China: potential for genetic reassortment? *J. Virol.* 75, 9679-9686.

Pumpens, P., and Grens, E. (2003). Artificial genes for chimeric virus-like particles. In: "Artificial DNA" (Khudyakov, Y. E, and Fields, H. A., Eds.) pp. 249-327. CRC Press, New York.

Pushko, P., Parker, M., Ludwig, G. V., Davis, N. L., Johnston, R. E., and Smith, J. F. (1997). Replicon-helper systems from attenuated Venezuelan equine encephalitis virus: expression of heterologous genes in vitro and immunization against heterologous pathogens in vivo. *Virology* 239, 389-401.

Slepushkin, V. A., Katz, J. M., Black, R. A., Gamble, W. C., Rota, P. A., and Cox, N. J. (1995). Protection of mice against influenza A virus challenged by vaccination with baculovirus-expressed M2 protein. *Vaccine* 13, 1399-1402.

Treanor, J. J., Betts, R. F., Smith, G. E., Anderson, E. L., Hackett, C. S., Wilkinson, B. E., Belshe, R. B., and Powers, D. C. (1996). Evaluation of a recombinant hemagglutinin expressed in insect cells as an influenza vaccine in young and elderly adults. *J. Infect. Dis.* 173, 1467-1470.

Tsuji, M., et al. (1998). Recombinant Sindbis viruses expressing a cytotoxic T-lymphocyte epitope of a malaria parasite or of influenza virus elicit protection against the corresponding pathogen in mice. *J. Virol.* 72, 6907-6910.

Ulmer, J. B., et al. (1993). Heterologous protection against influenza by injection of DNA encoding a viral protein. *Science* 259, 1745-1749.

Ulmer, J. B., et al. (1998). Protective CD4+ and CD8+ T cells against influenza virus induced by vaccination with nucleoprotein DNA. *J. Virol.* 72, 5648-5653.

Watanabe, T., Watanabe, S., Neumann, G., and Kawaoka, Y. (2002) Immunogenicity and protective efficacy of replication-incompetent influenza virus-like particles. *J. Virol.* 76, 767-773.

Zhou, X., et al. (1995). Generation of cytotoxic and humoral immune responses by non-replicative recombinant Semliki Forest virus. *Proc. Natl. Acad. Sci. USA* 92, 3009-3013.

Other Embodiments

Those skilled in the art will recognize, or be able to ascertain using no more than routine experimentation, many equivalents to the specific embodiments of the invention described herein. Such equivalents are intended to be encompassed by the following claims:

TABLE 1

| Fraction#* | Titer |
|---|---|
| 1 | <1:500 |
| 3 | <1:500 |
| 5 | 1:500 |
| 7 | 1:1000 |
| 9 | 1:2000 |
| 11 | 1:2000 |
| 12 | 1:4000 |
| 14 | 1:500 |
| 16 | <1:500 |
| PBS** | <1:500 |
| A/Shangdong/9/93*** | 1:1000 |

*Fractions from 20-60% sucrose gradient
**Negative control
***Positive control

TABLE 2

TABLE 2

| Virus | Strain | Gene | RT-PCR Primer |
|---|---|---|---|
| Type A (H3N2) | Sydney/ 5/97 | Hemag-glutinin (HA) | Forward 5'-A GGATCCATGAA<br>GACTATCATTGCTTTGAG-3'<br>(SEQ ID NO: 4)<br>Reverse 5'-A GGTACCTCAAAT<br>GCAAATGTTGCACCTAATG-3'<br>(SEQ ID NO: 5) |
| | | Neura-minidase (NA) | Forward 5'-GGGGACAAGTTTGT<br>ACAAAAAAGCAGGCTTAGAAGGAGA<br>TAGAACC ATG AATCCAAATCAAA<br>AGATAATAAC-3'<br>(SEQ ID NO: 6)<br>Reverse 5'-GGGGACCACTTTGT<br>ACAAGAAAGCTGGGTCCTATATAGG<br>CATGAGATTGATGTCCGC-3'<br>(SEQ ID NO: 7) |
| | | Matrix (MI) | Forward 5'-AAA GAATTC ATG<br>AGTCTTCTAACCGAGGTCGAAAC<br>GTA-3'(SEQ ID NO: 8)<br>Reverse 5'-AAA TTCGAA TTA<br>CTCCAGCTCTATGCTGAGAAAAT<br>GAC-3'(SEQ. ID NO: 9) |
| | | M2 | Forward 5'-A GAATTC ATG AG<br>TCTTCTAACCGAGGTCGAAACGCCT<br>ATCAGAAACGAATGGGGGTGC-3'<br>(SEQ ID NO: 10)<br>Reverse 5'-AAA TTCGAA TT<br>ACTCCAGCTCTATGCTGACAAAAT<br>GAC-3'(SEQ ID NO: 11) |
| | | Nucleo-protein (NP) | Forward 5'-A GAATTC ATG GC<br>GTCCCAAGGCACCAACG-3'<br>(SEQ ID NO: 12)<br>Reverse 5'-A GCGGCCGCTTAAT<br>TGTCGTACTCCTCTGCATTGTCTCCG<br>AAGAAATAAG-3'(SEQ ID NO: 13) |
| Type B | Harbin | Hemag-glutinin (HA) | Forward 5'-A GAATTC ATG AA<br>GGCAATAATTGTACTACTCATGG-3'<br>(SEQ ID NO: 14)<br>Reverse 5'-A GCGGCCGCTTATA<br>GACAGATGGAGCAAGAAACATTGTCT<br>CTGGAGA-3'(SEQ ID NO: 15) |
| | | Neura-minidase (NA) | Forward 5'-A GAATT CATG CT<br>ACCTTCAACTATACAAACG-3'<br>(SEQ ID NO: 16)<br>Reverse 5'-A GCGGCCGCTTACA<br>GAGCCATATCAACACCTGTGAC<br>AGTG-3'(SEQ ID NO: 17) |

The invention claimed is:

1. A method of preventing influenza in a vertebrate comprising administering a vaccine to the vertebrate, wherein the vaccine comprises:

i) a virus-like particle (VLP) comprising influenza structural proteins, wherein the influenza structural proteins of the VLP consist of M1, HA, and NA, wherein the VLP is self-assembled in a host cell from a recombinant construct wherein the M1 protein is from an avian influenza virus, and wherein the M1 protein is from a different strain of influenza virus than the influenza HA protein and the influenza NA protein; and ii) a carrier or diluent.

2. The method of claim 1 wherein the vaccine is a multivalent vaccine.

3. The method of claim 1, wherein the host cell is a eukaryotic cell.

4. The method of claim 3, wherein the eukaryotic cell is an insect cell.

5. The method of claim 3, wherein the recombinant construct is a recombinant baculovirus construct.

6. The method of claim 1, wherein the HA and NA proteins are derived from a mammalian influenza strain.

7. The method of claim 1, wherein the HA and NA proteins are derived from the group consisting of subtype A and B influenza viruses.

8. The method of claim 1, further comprising an adjuvant.

9. The method of claim 1 wherein the HA protein exhibits hemagglutinin activity.

10. The method of claim 1, wherein the NA protein exhibits neuraminidase activity.

* * * * *